US007063694B2

(12) United States Patent
Nahen et al.

(10) Patent No.: US 7,063,694 B2
(45) Date of Patent: Jun. 20, 2006

(54) METHOD AND SYSTEM FOR PHOTOSELECTIVE VAPORIZATION FOR GYNECOLOGICAL TREATMENTS

(75) Inventors: Kester Nahen, Mountain View, CA (US); Steven C. Murray, Santa Cruz, CA (US); Scott A. Davenport, Half Moon Bay, CA (US); Tony D. Coleman, San Jose, CA (US); Ken Arnold, Soquel, CA (US); Henry Garlich, Fremont, CA (US)

(73) Assignee: Laserscope, San Jose, CA (US)

( * ) Notice: Subject to any disclaimer, the term of this patent is extended or adjusted under 35 U.S.C. 154(b) by 45 days.

(21) Appl. No.: 10/371,080

(22) Filed: Feb. 21, 2003

(65) Prior Publication Data

US 2003/0216717 A1 Nov. 20, 2003

Related U.S. Application Data

(60) Provisional application No. 60/358,356, filed on Feb. 22, 2002.

(51) Int. Cl.
*A61B 18/20* (2006.01)

(52) U.S. Cl. .............................. 606/15; 128/898; 606/3; 606/13

(58) Field of Classification Search .............. 606/1–19; 600/104–108; 128/898
See application file for complete search history.

(56) References Cited

U.S. PATENT DOCUMENTS

| 4,402,569 A | 9/1983 | Bow et al. |
| 4,418,689 A | 12/1983 | Kanazawa |

(Continued)

OTHER PUBLICATIONS

Buttram, Veasy C., et al., "Indications for Myomectomy," Seminars in Reproductive Endocrinology 10(4) (Nov. 1992) 378–384.
Grabo, Theresa N., et al., "Uterine Myomas: Treatment Options," JOGNN 28(1) (Jan./Feb. 1999), 23–31.
Indman, Paul D., "Hysteroscopic Treatment of Menorrhagia Associated with Uterine Leiomyomas," Obstetrics & Gynecology 81(5) part 1 (May 1993), 716–720.
Indman, Paul D., et al., "Uterine Surface Temperature Changes Caused by Endometrial Treatment with the Nd:YAG Laser," J Reprod Med 36(7) (Jul. 1991), 505–512.
Indman, Paul D., "High–Power Nd:YAG Laser Ablation of the Endometrium," J Repro Med 36(7) (Jul. 1991), 501–504.
Chui, Carie T., M.D., et al., "Long–Pulsed Nd:YAG for Hair Removal: Early Histological Changes," LaserNews.net, LLC, 1999.

(Continued)

*Primary Examiner*—Roy D Gibson
*Assistant Examiner*—Henry M Johnson, III
(74) *Attorney, Agent, or Firm*—Mark A. Haynes; Haynes Beffel & Wolfeld LLP

(57) ABSTRACT

A method for photoselective vaporization of uterine tissue includes delivering laser radiation to the treatment area on the tissue, via an optical fiber for example, wherein the laser radiation has a wavelength and irradiance in the treatment area on the surface of the tissue sufficient because vaporization of a substantially greater volume of tissue than a volume of residual coagulated tissue caused by the laser radiation. The laser radiation is generated using a neodymium doped solid-state laser, including optics producing a second or higher harmonic output with greater than 60 watts average output power. The delivered laser radiation has a wavelength for example in a range of about 200 nm to about 650 nm, and has an average irradiance in the treatment area greater than about 10 kilowatts/cm$^2$, in a spot size of at least 0.05 mm$^2$.

106 Claims, 10 Drawing Sheets

U.S. PATENT DOCUMENTS

| | | | |
|---|---|---|---|
| 4,646,737 A | | 3/1987 | Hussein et al. |
| 4,722,337 A | | 2/1988 | Losch et al. |
| 4,760,840 A | * | 8/1988 | Fournier et al. ............... 606/15 |
| 4,802,461 A | | 2/1989 | Cho |
| 4,834,091 A | | 5/1989 | Ott |
| 4,836,189 A | | 6/1989 | Allred, III et al. |
| 4,907,235 A | | 3/1990 | Kuizenga |
| 4,944,738 A | | 7/1990 | Rodriguez |
| 4,981,138 A | | 1/1991 | Deckelbaum et al. |
| 5,025,446 A | | 6/1991 | Kuizenga |
| 5,147,353 A | * | 9/1992 | Everett ........................ 606/15 |
| 5,151,909 A | | 9/1992 | Davenport et al. |
| 5,231,641 A | | 7/1993 | Ortiz |
| 5,242,390 A | * | 9/1993 | Goldrath ..................... 604/515 |
| 5,243,615 A | | 9/1993 | Ortiz et al. |
| 5,249,192 A | | 9/1993 | Kuizenga et al. |
| 5,257,991 A | | 11/1993 | Fletcher et al. |
| 5,269,779 A | | 12/1993 | Sogawa et al. |
| 5,300,061 A | | 4/1994 | Easley et al. |
| 5,312,392 A | | 5/1994 | Hofstetter et al. |
| 5,380,317 A | | 1/1995 | Everett et al. |
| 5,409,481 A | | 4/1995 | Poppas et al. |
| 5,421,323 A | * | 6/1995 | Herrmann et al. .......... 600/108 |
| 5,428,699 A | * | 6/1995 | Pon ............................. 385/31 |
| 5,437,660 A | | 8/1995 | Johnson et al. |
| 5,449,354 A | * | 9/1995 | Konwitz et al. ............... 606/15 |
| 5,451,221 A | | 9/1995 | Cho et al. |
| 5,495,541 A | | 2/1996 | Murray et al. |
| 5,607,420 A | | 3/1997 | Schuman |
| 5,628,744 A | | 5/1997 | Coleman et al. |
| 5,632,739 A | | 5/1997 | Anderson et al. |
| 5,649,924 A | * | 7/1997 | Everett et al. ................ 606/15 |
| 5,662,646 A | | 9/1997 | Fumich |
| 5,733,279 A | | 3/1998 | Konwitz et al. |
| 5,746,760 A | | 5/1998 | Humphrey, Jr. |
| 5,772,658 A | | 6/1998 | Konwitz |
| 5,776,127 A | | 7/1998 | Anderson et al. |
| 5,776,175 A | | 7/1998 | Eckhouse et al. |
| 5,778,395 A | | 7/1998 | Whiting et al. |
| 5,798,518 A | | 8/1998 | Coleman et al. |
| 5,807,389 A | | 9/1998 | Gardetto et al. |
| 5,841,800 A | | 11/1998 | Davenport et al. |
| 5,843,026 A | | 12/1998 | Edwards et al. |
| 6,024,751 A | | 2/2000 | Lovato et al. |
| 6,064,914 A | | 5/2000 | Trachtenberg |
| 6,086,580 A | | 7/2000 | Mordon et al. |
| 6,164,280 A | * | 12/2000 | Everett et al. ............... 128/898 |
| 6,389,313 B1 | | 5/2002 | Marchitto et al. |
| 6,423,055 B1 | | 7/2002 | Farr et al. |
| 6,482,199 B1 | * | 11/2002 | Neev ........................... 606/10 |
| 6,554,824 B1 | | 4/2003 | Davenport et al. |
| 6,554,825 B1 | * | 4/2003 | Murray et al. ................ 606/11 |
| 6,699,239 B1 | | 3/2004 | Stiller et al. |

OTHER PUBLICATIONS

Cornford, P.A., et al., "Transurethral Incision of the Prostate Using the Holmium: YAG Laser: A Catheterless Procedure," The Journal of Urology, vol. 159, Apr. 1998, pp. 1229–1231, American Urological Association, Inc.

Gilling, Peter, J., et al., "Combination of Holmium and Nd:YAG Laser Ablation of the Prostate: Initial Clinical Experience," Journal of Endourology, vol. 9, No. 2, Apr. 1995, Mary Ann Liebert, Inc. Publishers.

Gilling, Peter, "Holmium Laser Resection of the Prostate Versus Neodymium: Yttrium–Aluminum–Garnet Visual Laser Ablation of the Prostate: Randomized Prospective Comparison of Two Techniques for Laser Prostatectomy," Urology, vol. 51, No. 2.

Gilling, Peter, J., et al., "Holmium Laser Versus Transurethral Resection of the Prostate: a Randomized Prospective Trial with 1–year Followup," The Journal of Urology, vol. 162, Nov. 1999, pp. 1640–1644, American Urological Association.

Hai, Mahmood A., et al., "Photoselective Vaporization of the Prostate in Treatment of Symptomatic Benign Prostatic Hyperplasia: Initial Experience," Abstract, Dept. of Urology, Oakwood Annapolis Medical Center, Detroit, MI.

Kollmorgen, Thomas A., et al., "Laser Prostatectomy: Two and a Half Years'Experience with Aggressive Multifocal Therapy," Urology, 48(2) 1996 217–222.

Kuntzman, Randall S., et al., "High–Power (60–Watt) Potassium–Titanyl–Phosphate Laser Vaporiztion Prostatectomy in Living Canines and in Human and Canine Cadavers," Urology, 49(5), pp. 703–708, Elsevier Science, Inc. 1997.

Kuntzman, Randall S., et al., "High–Power Potassium Titanyl Phosphate Laser Vaporization Prostatectomy," Mayo Clin Prac, 1998:73;798–801.

Kuntzman, Randall S., et al., "Potassium–Titanyl–Phosphate Laser Vaporization of the Prostate: A Comparative Functiional and Pathologic Study in Canines," Urology 48(4) 1996 575–583.

LaHaye, C.T.W., et al., "Optimal Laser Parameters for Port Wine Stain Therapy: A Theoretical Approach," Phys. Med. Biol., vol. 30, No. 6, pp. 573–587, 1985.

Landthaler, M., M.D., et al., "Effects of Argon, Dye, and Nd:YAG Lasers on Epideris, Dermis, and Venous Vessels," Lasers in Surgery and Medicine, vol. 6, pp. 87–93, Alan R. Liss, Inc., 1986.

Malek, Reza S., et al., "High Power Potassium–Titanyl–Phosphate Laser Vaporization Porstatectomy," The Journal of Urology, vol. 163, Jun. 2000, pp. 1730–1733, American Urological Association, Inc.

Malek, Reza S., et al., "High–Power Potassium–Titanyl–Phosphate (KTP/532) Laser Vaporization Prostatectomy: 24 Hours Later, " Urology, 51(2) pp. 254–256, Elsevier Science, Inc., 1998.

Malek, Reza S., et al., "KTP Laser Prostatecomy: Long–term Experience," can be found at www.laserscope.com.

Moretti, Michael, "Laserscope's Lyra Laser Proves Multi–Functional," Aesthetic Buyers Guide, Medical Insight, Inc., Jul. 2000.

Mottet, Nicolas, M.D., PH.D. et al., "Randomized Comparison of Transurethral Electroresection and Holmium: YAG Laser Vaporization for Symptomatic Benign Prostatic Hyperplasia," Journal of Endourology, vol. 13, No. 2, Mar. 1999, pp. 127–130, Mary Ann.

Rosenfeld, Harold, et al., "Treatment of Cutaneous and Deep Vascular Lesions with the Nd:YAG Laser," Lasers in Surgery and Medicine, vol. 6, pp. 20–23, 1986.

Schneider, Ellen Meyer, "Try Different Lasers for Treating Blood Vessel Disorders," Cosmetic Surgery Times, Oct. 1999.

Svelto, Orazio, "Principles of Lasers," Fourth Ed., pp. 480–482, Plenum Press, New York, NY, 1998.

Van Gemert, Martin J.C. PH.D., et al., "Treatment of Port–Wine Stains: Analysis" Medical Instrumentation, vol. 21, No. 4, pp. 213–217, Association for the Advancement of Medical Instrumentation, 1987.

Van Gemert, Martin J.C., PH.D., et al., "Is There an Optimal Laser Treatment for Port Wine Stains?", Lsers in Surgery and Medicine, vol. 6, pp. 76–83, Alan R. Liss, Inc.

Van Swol, Chirsitaan F. P. et al., "Physical Evaluation of Laser Prostatectomy Devices," Laser in Urology, Eds. Watson GM, Steiner RW and Johnson DE, SPIE Bellingham, vol. 2129, 1994.

Zelickson Brian D., M.D., et al., "Preliminary Results of the Lyra Long Pulsed Nd:YAG Laser Treatment of Leg Veins," Abstract of Presentation by Dr. brian Zelickson at the ISCLS in May 2000.

"The Lyra Laser System from Laserscope" Long–pulse Nd:YAG Laser Proven in Cosmetic Treatments, Medco Forum, vol. 7, No. 2, Mar. 2000.

"Laserscope Accounces FDA Clearance for Pseudo–Folliculitis," Laserscope.com/news/021401. htm, Feb. 14, 2001. p. 1–2.

"Laserscope Announces PMA Application to U.S. Food and Drug Administratio for PDT Treatment of Head and Neck Cancer," Laserscope.com/news/110999.htm, Nov. 9, 1999, pp. 1–2.

"Laserscope Encouraged by Clinical Study Using New Lyra Laser System to Treat Leg Veins," Laserscope.com/news/120799.htm, Dec. 7, 1999, pp. 1–2.

"Laserscope Announces High Power Lyra Laser System: Lyra XP, AAD to be Introduced at the ADD," Laserscope.com/news/030800.htm, Mar. 8, 2000, pp. 1–2.

"Laserscope Receives FDA Clearance ot Market New Lyra Laser System for Hair Removal: First laser Designed for Full Range of Skin Types," Laserscope.com/new031300.htm, Mar. 13, 2000.

"Laserscope Reprts First Quarter 2000 Results," Laserscope.com/news/050400.htm, May 4, 2000, p. 103.

"Laserscope Announces Approvable Letter Received for PDT Laser System for the Treatment of Head and Neck Cancer," Laserscope.com/news/052200.htm, May 22, 2000, p. 102.

"Researchers Report Decidely Positive Tow–Year Results Using Laserscope's Ultra–High Power Laser and Disposable Fiber Optics to Treat BPH: Researchers Call the Results Unprecedented," Laserscope.com/news/060800.htm, Jun. 8, 2000, pp. 1–2.

"Laserscope Announces a Winner of the Palm Pilot Drawing," Laserscope.com/news/100300.htm, Sep. 29, 2000, p. 1.

"Laserscope Reports Increased Profits in Third Quarter 2000 Results," Laserscope.com/news/101900.htm, Oct. 19, 2000, pp. 1–3.

"Laserscope Signs Exclusive Agreement with McKessinH-BOC Medical Group for National Distribution of Aesthetic Laser Systems," Laserscope.com/news/121400.htm, Dec. 14, 2000, pp. 1–2.

"Laserscope Reports Fourth Quarter and Year End 2000 Results," Laserscope.com/news/021301 htm, Feb. 12, 2001, pp. 1–3.

"Niagara PV System: Breakthrough Technology for the Treatment of BPH," http://www.laserscope.com/professionals/urology/niagara.html.

"Niagara PVP Procedure: Photoselective Vaporization of the Prostate v. TURP: Transurethral Resection of the Prostate," http://www.laserscope.com/professionals/urology/clinicalstudies.html.

"Niagara PVP Procedure(Photoselective Vaporization of the Prostate) vs. Other Treatment Options," http://www.laserscope.com/professionals/urology/clinicalstudies.html.

Dixon J.A., "Argon and Neodymium YAG Laser Therapy of Dark Nodular Port Wine Stains in Older Patients," Lasers in Surgery and Medicine 6:5–11 (1986).

* cited by examiner

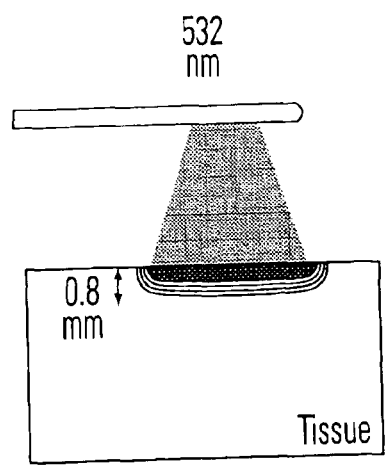
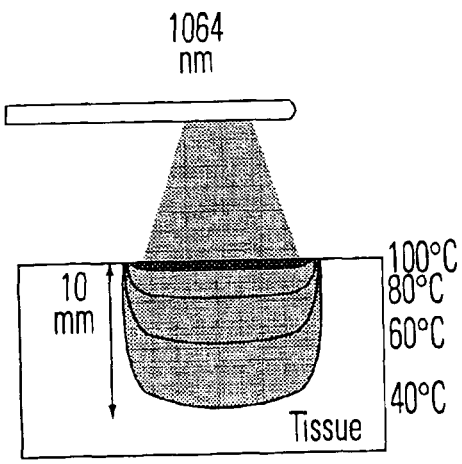
FIG. 8  FIG. 9
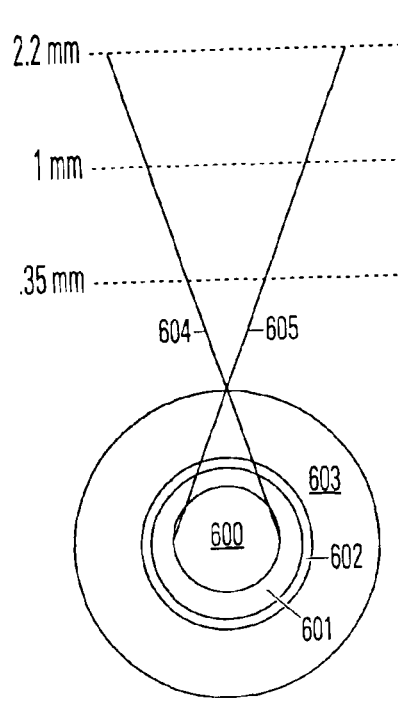
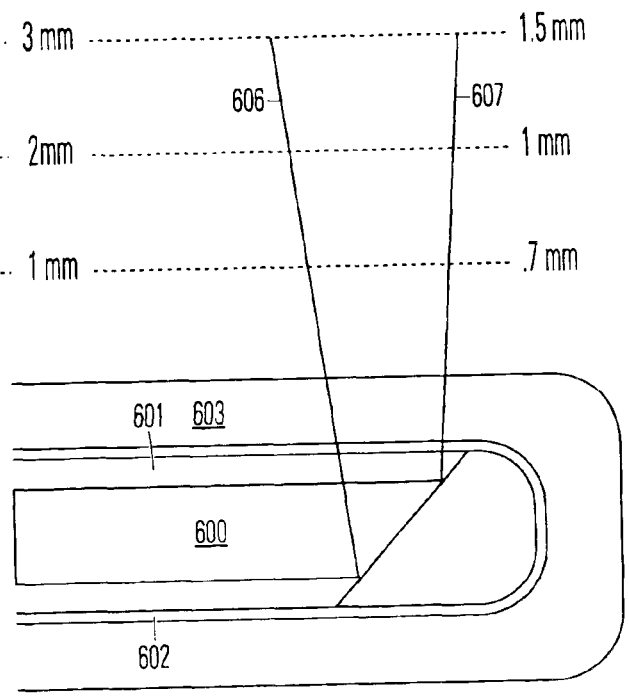
FIG. 10  FIG. 11

METHOD AND SYSTEM FOR PHOTOSELECTIVE VAPORIZATION FOR GYNECOLOGICAL TREATMENTS

RELATED APPLICATION INFORMATION

The present invention claims the benefit of U.S. Provisional Application No. 60/358,356, entitled METHOD FOR TREATMENT OF GYNECOLOGICAL CONDITIONS USING A HIGH POWER LASER IN CONJUNCTION WITH A HYSTEROSCOPE, filed 22 Feb. 2002.

The present application is related to, and incorporates by reference as if fully set forth herein, U.S. patent application Ser. No. 10/278,723, entitled METHOD AND SYSTEM FOR PHOTOSELECTIVE VAPORIZATION OF THE PROSTATE, AND OTHER TISSUE, filed 23 Oct. 2002;

U.S. patent application Ser. No. 09/737,721, entitled METHODS FOR LASER TREATMENT OF SOFT TISSUE, filed 15 Dec. 2000; and U.S. patent application Ser. No. 10/279,087, entitled METHOD AND SYSTEM FOR TREATMENT OF BENIGN PROSTATIC HYPERTROPHY (BPH), invented by Murray, et al.; filed: 23 Oct. 2002

BACKGROUND OF THE INVENTION

1. Field of the Invention

The present invention relates generally to laser treatment of tissue, and more particularly to photoselective vaporization of tissue, including uterine tissue, as applied to the treatment of gynecological conditions.

2. Description of Related Art

A commonly employed procedure for removal of tissue in the treatment of gynecological conditions involves the use of a hysteroscope and a small wire loop energized by radio frequency energy to cut tissue.

Nd:YAG lasers delivering output with a wavelength of 1064 nm have been used for the treatment of gynecological conditions such as the ablation of the endometrium. Although 1064 nm light is hemostatic at high power levels, its low absorption in blood and uterine tissue leads to inefficient ablation and a large residual layer of thermally denatured tissue several millimeters thick.

High power densities are required for rapid and efficient vaporization of tissue. The difficulty of achieving higher average output power densities is that when high input powers are supplied to the laser element from an excitation source such as an arclamp a large amount of heat is generated in the lasing element. This heat induces various deleterious effects in the lasing element. In particular the temperature difference between the coolant and the hot lasing element generates a thermally induced graded index lens that decreases the beam quality of the laser and causes the laser to operate with more transverse optical modes than it would otherwise.

The $M^2$ parameter is a well established convention for defining the beam quality of a laser and is discussed in pages 480–482 of Orazio Svelto and David C. Hanna, *Principles of Lasers*, Plenum Press, New York, 1998, which is incorporated herein by reference. The beam quality measures the degree to which the intensity distribution is Guassian. The quantity $M^2$ is sometimes called inverse beam quality rather than beam quality but in this application it will be referred to as beam quality. $M^2$ is defined as $$M_x^2 \equiv \frac{(\sigma_x \sigma_f)_{NG}}{(\sigma_x \sigma_f)_G} = 4\pi(\sigma_x \sigma_f)_{NG},$$

where $\pi$ refers to the number 3.14 . . . , $\sigma$ is used to represent the spot size, the subscripts x and f represent the spatial and frequency domains along the x-axis, respectively, and the subscripts G and NG signify Guassian and non-Guassian, respectively. The x-axis is transverse to the direction of propagation of the beam. The beam quality in any direction transverse to the beam may be essentially the same. Therefore the subscript x is dropped from the $M^2$ elsewhere in the specification. The beam widths or $\sigma$s are determined based on the standard deviation of the position, where the squared deviation of each position is weighted by the intensity at that point. The beam width in the frequency domain $\sigma_f$ is the beam width of the beam after being Fourier transformed.

The formula usually used for calculating the angular divergence, $\theta$, of a beam of light of wavelength $\lambda$ is strictly valid only for a beam having a Guassian intensity distribution. The concept of beam quality facilitates the derivation of the angular divergence, $\theta$, for the beam with a non-Guassian intensity distribution, according to $$\theta = M^2\left(\frac{2\lambda}{\pi\sigma_x}\right).$$

For example, a TEM00 laser beam has a high beam quality with an $M^2$ of 1, whereas by comparison, high power surgical lasers operate with $M^2$ values greater than 100.

The Applicants have recognized that high power lasers typically have an $M^2 > 144$. The larger number of modes makes $M^2$ larger and makes it difficult to focus the light into small, low numerical aperture fibers and reduces the ability to project high power density light onto tissue. As a result, the vaporization efficiency of CW arclamp pumped 532 nm lasers is significantly reduced.

Surgical procedures within the uterus have unique risks. For example, precision surgery is of high importance for patients who want to maintain their fertility. Any surgery in the uterus must avoid weakening of the wall of the uterus, which could lead to complications during pregnancy. Also, the physiological diversity of the uterus increases the difficulty of intrauterine operations. The cornual areas of the uterus represent a vulnerable portion of the uterus. In case of a myoma in the cornu, the uterine wall is further thinned by the myoma, which increases the risk of intraoperative perforation of the uterine wall. Even if perforation does not occur, the presence of a thin uterine wall could predispose the patient to bowel injury. As stated by Indman, J. Reprod-uct. Med. 1991, lack of precise knowledge of the minimum thickness of the uterine wall may be the limiting factor in determining the safety of use of the 1064 nm Nd:YAG laser for endometrial ablation.

SUMMARY OF THE INVENTION

Photoselective vaporization of tissue, such as tissue subject of removal for treatment of gynecological conditions, is based upon applying a high intensity radiation to tissue using a radiation that is highly absorptive in the tissue, while being absorbed only to a negligible degree by water or other irrigant during the operation, at power densities such that the majority of the energy is converted to vaporization of the tissue without significant residual coagulation of adjacent tissue.

The present invention provides a method for treating gynecologic conditions, including conditions involving uterine tissue, such as intramural and intracavitery uterine myomas, leiomyoma uteri, rhabdomyoma, endometriosis, endometrial hyperplasia, endometrial cysts, endometrial polyps, menorrhagia, uterine septa, intrauterine adhesions, or cervical intraepithelial neoplasia. Other gynecological conditions involving the female reproductive organs such as the fallopian tubes, the ovaries, and the vagina, are also treatable according to the present invention. Treatment according to the embodiments of present invention is executed by vaporizing, incising, or coagulating tissue, such as uterine tissue, using a laser that generates light with an average power greater than 40 watts and a wavelength between 300 and 700 nm where the output beam of the laser is delivered to the target tissue through an optical waveguide, such as an optical fiber that emits light in forward direction (end-firing) or in a laterally directed manner (side-firing) where laterally means at an angle of 10°–170° with respect to the fiber axis, and where the waveguide is guided into the vagina or the uterine cavity using a hysteroscope. In embodiments of the invention, the hysteroscope is equipped with a rigid tip. In other embodiments of the invention, the hysteroscope is equipped with a flexible tip, which can be manipulated by the surgeon, allowing greater control over the procedure, and access to more regions of the target tissue.

In other embodiments, the wavelength of the delivered radiation is between 1100 and 1800 nm, or in other bands that are efficiently absorbed by the target tissue.

Yet other embodiments employ a laser system, that generates light of two wavelengths, with for example two lasers arranged to provide light to a beam delivery system, with the light of the first wavelength having an average power greater than 40 watts, and in some embodiments more than 60 Watts, and a wavelength between 300 and 700 nm, such as a wavelength of 532 nm, and the light of the second wavelength having a wavelength of 1064 nm. In alternative one or two wavelength systems, delivered light is between 1100 and 1800 nm.

According to one embodiment of the invention, a method for treating gynecological conditions comprises the steps of providing a solid-state laser having a laser element positioned to receive pump radiation from an excitation source; in some cases modulating the source to cause the laser to emit pulsed laser light; and delivering the laser light to targeted tissue. Various solid-state lasers may be used for this purpose, including (without limitation), a Q-switched laser using a frequency doubling crystal such as potassium-titanyl-phosphate (KTP), pumped using a diode array, an arc lamp or a flash lamp. While Q-switching induces short, "micro-pulses," a "macro-pulse" duration of the laser light is preferably in the range of 0.1 to 500 milliseconds, induced by for example modulating the pump energy with the desired macro-pulse length. The wavelength of the laser light is preferably between 200 and 1000 nm, and more preferably between about 300 and 700 nm. The laser light is preferably delivered to the targeted tissue through an optical fiber terminating at or near a distal end in a side-firing or end-firing probe.

Operation of the solid-state laser in a "macro-pulsed" mode is more efficient in vaporizing tissue than a CW laser of the same average power. This is in part because the heat generated in a superficial tissue layer, which depth is defined by the optical penetration depth of the laser beam, doesn't have time to significantly diffuse into deeper tissue layers during each macro pulse. The heat stays confined in the superficial tissue layer and leads to a rapid heating of the tissue to the boiling point of water. The thermal energy generated within a tissue volume has to exceed the vaporization enthalpy of water to fully vaporize the tissue. For a laser operated in a macro-pulsed mode this condition is met for a larger tissue volume than for a laser operated in a continuous mode. The macro-pulsed laser is also more efficient and has higher beam quality, with M2 values typically less than 144, than a continuous wave laser with same average output power. The higher beam quality allows for higher irradiances on the tissue and thus a more rapid tissue vaporization.

According to a second embodiment of the invention, a method for treating uterine tissue comprises the steps of providing a solid-state laser having a laser element positioned to receive pump radiation from a pump radiation source; modulating the pump radiation source to cause the laser element to emit laser light having a pulse duration of between 0.1 milliseconds and 500 milliseconds and an average output power exceeding 20 watts; and delivering the laser light to targeted tissue.

According to a third embodiment of the invention, a method for treating gynecological conditions comprises the steps of providing a solid-state laser having a laser element positioned to receive pump radiation from a pump radiation source; Q-switching the laser to generate a quasi-continuous wave (CW) beam having an average output power exceeding 60 watts; and, delivering the beam to targeted tissue.

According to a fourth embodiment of the invention, a method for treating gynecological conditions comprises the steps of providing a solid-state laser having a laser element positioned to receive pump radiation from a pump radiation source such as a laser diode; Q-switching the laser to generate a quasi-continuous wave (CW) beam having an average output power exceeding 20 watts with an $M^2$ less than 144; and delivering the beam to uterine tissue.

It has been recognized that as more and more laser energy is consumed by vaporization of the tissue, the amount of laser energy leading to residual tissue coagulation gets smaller, i.e. the amount of residual coagulation drops, and the side effects attendant to the residual injury caused by the surgery drop dramatically. Thus, the extent of the zone of thermal damage characterized by tissue coagulation left after the procedure gets smaller with increasing volumetric power density, while the rate of vaporization increases. Substantial and surprising improvement in results is achieved. It has been recognized that increasing the volumetric power density absorbed in the tissue to be ablated, has the result of decreasing the extent of residual injury of the surrounding tissue. This recognition leads to the use of higher power laser systems, with greater levels of irradiance at the treatment area on the tissue, while achieving the lower levels of adverse side effects and a quicker operation times.

Although the invention can be generalized other types of tissue, one embodiment of the invention provides a method for photoselective vaporization of uterine tissue, including for example the endometrium and myomas in the uterine wall. According to this embodiment, the method includes delivering laser radiation to the treatment area on the tissue, via an optical fiber for example, wherein the laser radiation has a wavelength and irradiance in the treatment area on the surface of the tissue sufficient because vaporization of a substantially greater volume of tissue than a volume of residual coagulated tissue caused by the laser radiation. In one embodiment, the laser radiation is generated using a neodymium doped solid-state laser, including optics producing a second or higher harmonic output with greater than 60 watts average output power, and for example 80 watts average output power, or more. The laser radiation is coupled into an optical fiber adapted to direct laser radiation from the fiber to the treatment area on the surface of the tissue. For the treatment within the uterus, the fiber optic is inserted via hysteroscope, including lumens for delivering irrigants to the treatment area, and for direct visualization during the treatment. For treatment in the uterine cornua, or other difficult to reach regions, and more generally because of physiological diversity in the uterus, a flexible tip hysteroscope is used in embodiments of the present invention.

In other embodiments, the delivered laser radiation has a wavelength in a range of about 300 nm to about 700 nm, and has an average irradiance in the treatment area greater than about 10 kilowatts/cm$^2$, in a spot size of at least 0.05 mm$^2$. More preferably, the irradiance is greater than about 20 kilowatts/cm$^2$, and even more preferably greater than about 30 kilowatts/cm$^2$. The spot size in preferred systems is for example less than about 0.8 mm$^2$.

Accordingly, in one embodiment, the second harmonic output of the neodymium dope solid-state laser is applied using an optical fiber with a flat tip for emitting radiation from the end, or with a side-firing tip. When using a side-firing tip, which causes a diverging beam to be directed out of the optical fiber, the time is placed close to the tissue, within about 1 mm from the side of the side-firing tip to contacting the side of the tip. Close placement increases the irradiance delivered to the treatment area so that higher irradiance is available with solid-state lasers generating a 60 to 80 watts average output power.

According to the present invention, the efficiency of the vaporization and the reduction of injury to residual tissue are sufficient that the procedure may be carried out while applying less anesthesia during the delivery of laser energy, and throughout the procedure, than during other procedures. Anesthesia options for a procedure according to the present invention include, but are not limited to, paracervical block, and general or regional anesthesia techniques.

Furthermore, embodiments of the invention include the delivery of the laser energy using a Q-switched, solid-state laser which produces micro-pulses in combination with applying pump power to the laser medium in a sequence a pulses so that output radiation is produced in macro-pulses having a peak power of greater than 200 watts, and more preferably about 240 watts or greater. The peak irradiance in the treatment area during the pulses is thereby substantially increased, and preferably greater than 50 kilowatts/cm$^2$, and as much as 90 kilowatts/cm$^2$ in some embodiments of the invention.

Other aspects and advantages of the present invention can be seen on review the figures, the detailed description, and the claims which follow.

BRIEF DESCRIPTION OF THE DRAWINGS

FIG. 8 illustrates absorption depth in tissue for 532 nm light.

FIG. 9 illustrates absorption depth in tissue for 1064 nm light.

FIG. 10 is a diagram of a beam path from an end view of a side firing tip, according to one embodiment of the present invention.

FIG. 11 is a diagram of a beam path from a side view of the side firing tip of FIG. 10, according to one embodiment of the present invention.

DETAILED DESCRIPTION

Figure 1:
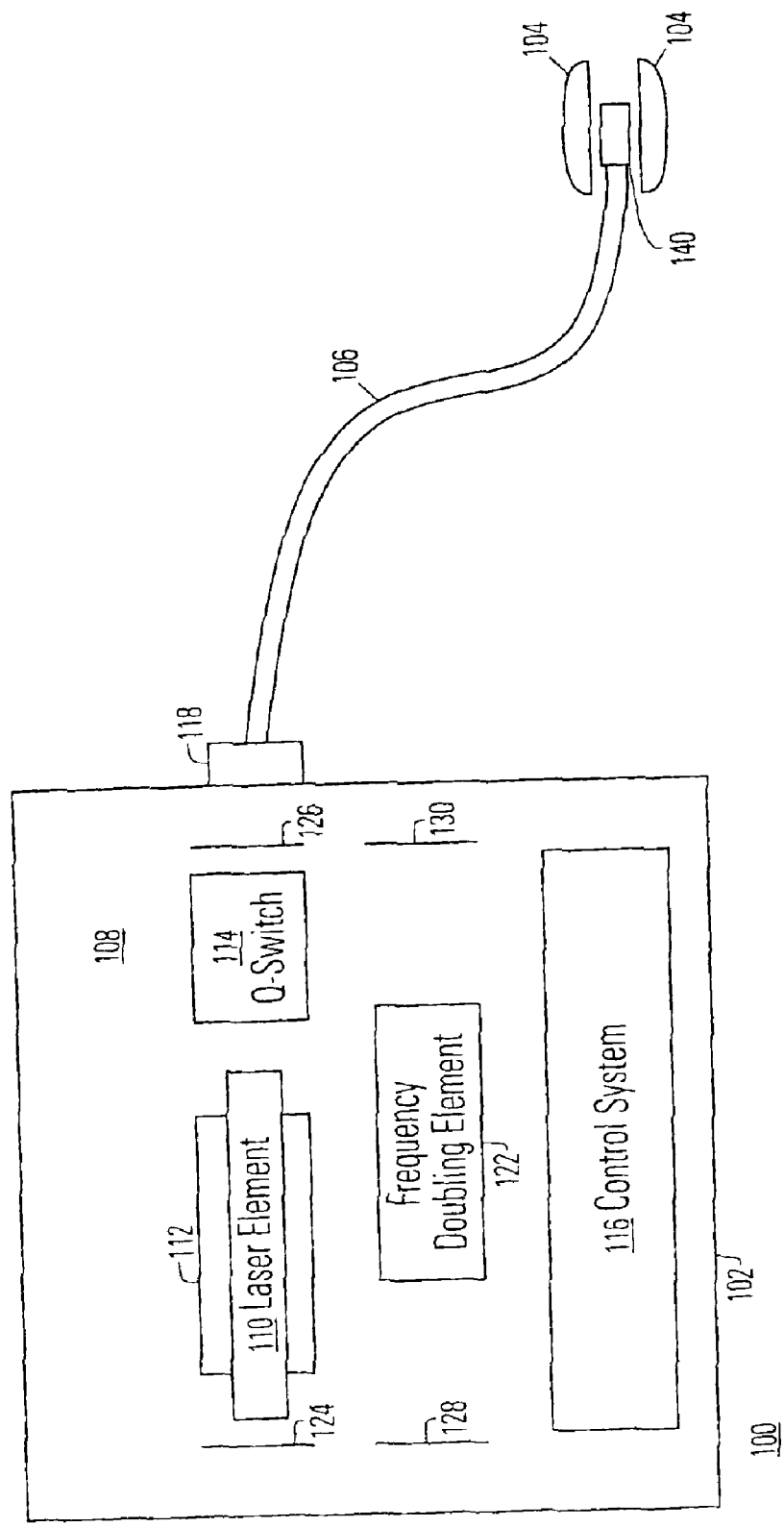
FIG. 1 depicts a laser system for implementing the tissue ablation methods of the invention.

FIG. 1 is a block diagram depicting an exemplary laser system 100 which may be employed for implementing the present invention. Laser system 100 includes a solid-state laser 102, which is used to generate laser light for delivery through optical fiber 106 to target tissue 104. As will be discussed in further detail herein below, laser 102 is capable of being operated in a "macro-pulsed" mode, wherein the laser light is emitted as macro-pulses having relatively long pulse durations.

Laser 102 more specifically comprises a laser element assembly 110, pump source 112, and frequency doubling crystal 122. In the preferred embodiment, laser element 110 outputs 1064 nm light which is focused into frequency doubling crystal 122 to create 532 nm light. According to one implementation, laser element assembly 110 may be neodymium doped YAG (Nd:YAG)crystal, which emits light having a wavelength of 1064 nm (infrared light) when excited by pump source 112. Laser element 110 may alternatively be fabricated from any suitable material wherein transition and lanthanide metal ions are disposed within a crystalline host (such as YAG, Lithium Yttrium Fluoride, Sapphire, Alexandrite, Spinel, Yttrium Orthoaluminate, Potassium Gadolinium Tungstate, Yttrium Orthovandate, or Lanthanum Scandium Borate). Laser element 110 is positioned proximal to pump source 112 and may be arranged in parallel relation therewith, although other geometries and configurations may be employed.

Pump source 112 may be any device or apparatus operable to excite laser element assembly 110. Non-limiting examples of devices which may be used as pump source 112, include: arc lamps, flashlamps, and laser diodes.

A Q-switch 114 disposed within laser 102 may be operated in a repetitive mode to cause a train of micro-pulses to be generated by laser 102. Typically the micro-pulses are less than 1 microsecond in duration separated by about 40 microseconds, creating a quasi-continuous wave train. Q-switch 114 is preferably of the acousto-optic type, but may alternatively comprise a mechanical device such as a rotating prism or aperture, an electro-optical device, or a saturable absorber.

Laser 102 is provided with a control system 116 for controlling and operating laser 102. Control system 116 will typically include a control processor which receives input from user controls (including but not limited to a beam on/off control, a beam power control, and a pulse duration control) and processes the input to accordingly generate output signals for adjusting characteristics of the output beam to match the user inputted values or conditions. With respect to pulse duration adjustment, control system 116 applies an output signal to a power supply (not shown) driving pump source 112 which modulates the energy supplied thereto, in turn controlling the pulse duration of the output beam.

Although FIG. 1 shows a frequency doubled laser with an intracavity frequency doubling element, it is only by way of example. The infrared light can be internally or externally frequency doubled using non-linear crystals such as KTP, Lithium Triborate (LBO), or Beta Barium Borate (BBO) to produce second harmonic 532 nm green light, and higher harmonics. The frequency doubled, 532 nm wavelength and the shorter wavelength higher harmonic beams are better absorbed by the tissue, and promote more efficient tissue ablation.

In one preferred embodiment the resonant cavity control system is that described in U.S. Pat. No. 5,151,909, which is incorporated by reference as if fully set forth herein.

Laser 102 further includes an output port couplable to optical fiber 106. Output port 118 directs the light generated by laser 102 into optical fiber 106 for delivery to tissue 104. Mirrors 124, 126, 128, and 130 direct light from the lasing element 110 to the frequency doubling crystal 122, in addition to forming the resonant cavity of the laser. Mirrors 124, 126, 128, and 130 are configured for focusing the light to form an image just in front of the frequency doubling crystal 122 on the side closer to mirror 130, and to compensate for thermal lensing in the lasing element. Although mirrors 124, 126, 128, and 130 are illustrated as flat and parallel to the walls of the laser, typically the focusing is achieved by curving and/or angling the mirrors. Alternatively transmissive optical elements could be used to focus the light and compensate for the thermal imaging. Mirrors 124, 128 and 130 reflect both the wavelength of light produced by the lasing element (e.g. 1064 nm) and the wavelength of the frequency doubled light (e.g. 532 nm). Mirror 126 only reflects the light originating from the lasing element 110 (e.g. 1064 nm) but is transparent to the frequency doubled light (e.g. 532 nm), forming an output window. Higher harmonic outputs may also be generated from the 1064 nm line, or other line amplified in the laser, including third and fourth harmonics, for shorter wavelengths. Other laser systems may be used, including but not limited to Sapphire lasers, diode lasers, and dye lasers, which are adapted to provide the output power and wavelengths described herein, including wavelengths in the ranges from 200 nm to 1000 nm and from 1100 nm to 1800 nm, for example.

While a bare fiber may be utilized for certain procedures, optical fiber 106 preferably terminates in a tip 140 having optical elements, or otherwise adapted, for shaping and/or orienting the beam emitted by optical fiber 106 so as to optimize the tissue ablation process.

Figure 2:
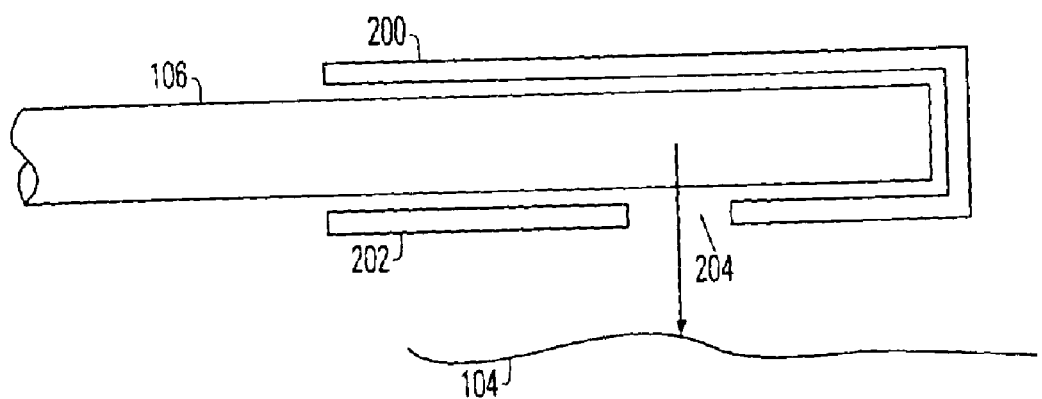
FIG. 2 depicts a side-firing probe for use with the system of FIG. 1.

FIG. 2 depicts a side-firing probe tip 200, which may be used as tip 140 (FIG. 1). The tip 140 is treated to deflect light sideways. Some examples of methods for deflecting the light sideways are to include a light scattering material in the tip 140 and/or to place a reflective element in the tip 140. The reflective element could be angled at 45°, for example; to deflect the light at 90° with respect to the axis of the fiber 106. Side-firing probe tip 200 includes an optically transparent sleeve 202 having a transparent window 204 (which may be constructed as a cutout in the wall of sleeve 202 through which the beam is emitted in a direction transverse to the optical axis of fiber 106.) An acceptable range of angles in which to deflect the light beam is between about 40 to 120 degrees with respect to the axis of the fiber. The preferred embodiments use an angle of either 70 or 100. The angle of 80° is preferred from the standpoint of the ease in manufacturing the tip 200 and the angle of 90° is preferred from the standpoint of the ease in aiming the side firing light.

In a typical mode of operation, optical fiber 106 is held within an endoscope such as a hysteroscope or similar instrument that allows the clinician to precisely position the distal end of the optical fiber adjacent to the targeted tissue. The endoscope also has channels for supplying and removing an irrigant solution to and from the tissue. In addition, light and image guides are also included for illuminating and imaging the tissue so that the clinician may direct the laser light and assess the progress and efficacy of the ablation procedure. Physiologic saline solution, typically containing 0.9% sodium chloride, is used as the irrigant in gynecological procedures according to the present invention.

Figure 3:
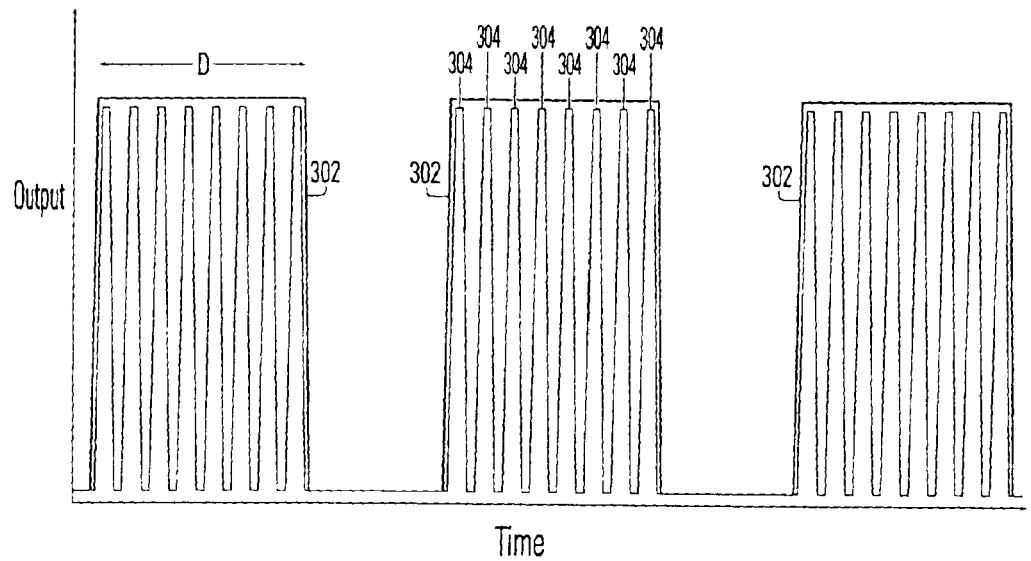
FIG. 3 depicts an exemplary output waveform of the FIG. 1 laser when the laser is operated in a macro-pulsed mode.

FIG. 3 illustrates an exemplary output waveform applied to tissue 104 when laser 102 is operated in the macro-pulsed mode. Each macro-pulse 302 is defined by a train of Q-switched micro-pulses 304. While a relatively small number of micro-pulses 302 are depicted for purposes of clarity, an actual macro-pulse may comprise hundreds or thousands of component micro-pulses 304. In the preferred embodiment there are between 2 and 12,200 micro-pulses per macro-pulse.

An arc lamp, for example, when used as the pump source 112, is kept at a low power level between pulses that are preferably just enough to maintain the arc. These low pump powers are below the lasing threshold of the laser; as a consequence, there is no laser output between macro-pulses.

As mentioned above, the pulse duration or width D (FIG. 3) of the output beam is governed by the modulation of pump source 112, and more specifically by the period during which the pump source 112 is maintained in an "on" or high-power condition. In other words, the longer the pump source 112 is maintained in an on condition, the longer the pulse width. Typically, laser 102 will be capable of delivering pulses 302 having pulse durations D in the range of 1 to 20 milliseconds (2 to 490 micro-pulses) or 1 to 50 milliseconds (2 to 1,220 micro-pulses) and average output powers preferably exceeding 60 watts and preferably up to 100 or 200 watts. The ratio of D to the period of the macro-pulses defines the duty cycle, which is typically between 10 and 50%.

In accordance with one embodiment of the invention, a laser system 100 of the foregoing description is employed to treat gynecological conditions by ablating targeted tissue 104. The clinician may utilize an endoscope or similar instrument to guide the distal end and tip 140 of optical fiber 106 into alignment with the targeted tissue 104. Laser system 100 is then operated in the macro-pulsed mode so that laser 102 generates laser light having the pulsed waveform depicted in FIG. 3 and delivers it through optical fiber 106 to tissue 104.

Prior art techniques for treatment of gynecological conditions by laser ablation (such as the technique described by Indman. in "High-Power Nd:YAG Laser Ablation of the Endometrium," *Journal of Reproductive Medicine*, Vol. 36, No.7, July 1991)) utilized an Nd:YAG laser to irradiate the uterine tissue. Although such lasers do produce moderately high average powers, they have a large number of transverse modes and as such, produce highly divergent light when focused into small fiberoptics. Further, the 1064 nm wavelength is less efficiently absorbed in the target tissue, that the wavelengths desirable according to the present invention. These characteristics of prior art 1064 nm systems lead to less than optimal power densities when the laser light is directed at tissue. As a consequence, ablation rates are relatively slow, significantly lengthening procedure times. Further, undesirable thermal damage to deeper tissue layers may occur. In contrast, it has been found that a macro-pulsed beam, such as that generated by laser 102, helps to accelerate ablation rates and reducing procedure time.

The macropulsing can also increase efficiency because the threshold voltage required for lasing while macropulsing (the operating threshold) is lower than the initial threshold voltage for lasing (cold threshold).

Macropulsing is also more efficient for producing green light because the conversion of infrared light to frequency doubled light increases as the square of the infrared light intensity. The higher peak powers of the macro-pulsed infrared light leads to higher second harmonic conversion efficiency. For example, at any given time, the input power and output power of a frequency-doubled laser using KTP are related according to $$Po = A(Pi)^2,$$

Where A is an experimentally determined positive constant. This equation relates the peak input power to the peak output power. However, the average input power and output power for a duty cycle of k percent are given by $$\langle Pi \rangle = k(Pi) \text{ and}$$

$$\langle Po \rangle = k(Po) = kA(Pi)^2 = A(\langle Pi \rangle)^2/k,$$

where the brackets "< >" indicate an average value of the enclosed quantity. Thus, decreasing the duty cycle from 100% to 50% (i.e. reducing k from 1 to 0.5) while simultaneously doubling the peak input power Pi results in no change to the average input power <Pi> and a doubling of the average output power <Po>. Pulse modulating or macropulsing using Q-switching, for example, enables reaching higher average output powers with less thermal lensing due to the lower input power.

Additionally, it is possible that the frequency doubling crystal has nonlinearly increasing output power as a function of the input power. In other words the second derivative of the output power with respect to the input power may be positive, in which case the rate of increase of the output power increases with increasing input power. Specifically, in such a case the functional dependence of the instantaneous or peak output power, Po, on the instantaneous or peak input power, Pi, is such that $$d^2(Po)/d(Pi)^2 > 0.$$

When this is true, and Po is an increasing function of Pi, the higher peak input power results in a more efficient laser because ratio of the output to input power increases.

Pump source modulation of the laser can produce high peak power macro-pulses and affect the efficiency of the average power output. Macro-pulse in excess of a steady state power can substantially improve the initiation of the vaporization of tissue. The higher peak power of the macropulse rapidly may initiate charring which in turn serves as an additional chromophore for the incident energy and enhances the vaporization rate. A 30% macro-pulse duty cycle is sufficient to increase the average power output of an arc lamp pumped laser to greater than 80 watts. Additionally the pump modulation generates macro-pulse with pulse powers greater than 240 watts.

By way of a non-limiting example, tissue 104 may be efficiently and rapidly ablated when laser 102 is operated at an output power of 80 to 100 watts, a pulse duration of 1–50 milliseconds, and a wavelength of 532 nm.

In accordance with a second method embodiment of the invention, laser system 100 may be utilized to ablate other types of tissue 104 involved in gynecological conditions. The clinician may utilize an endoscope or similar instrument to guide the distal end and tip 140 of optical fiber 106 into alignment with the tissue 104. Laser system 100 is then operated in the macro-pulsed mode so that laser light having the pulsed waveform depicted in FIG. 3 is generated by laser 102 and delivered through optical fiber 106 to tissue 104. To achieve adequate results, laser system 100 is adjusted to emit a beam having a pulse duration between 0.1 and 500 milliseconds, and an output power of at least 20 watts. Upon vaporization of the required volume of tissue 104, (which may be assessed via an imaging channel contained in the endoscope), the output beam of laser 102 is turned off.

Figure 4:
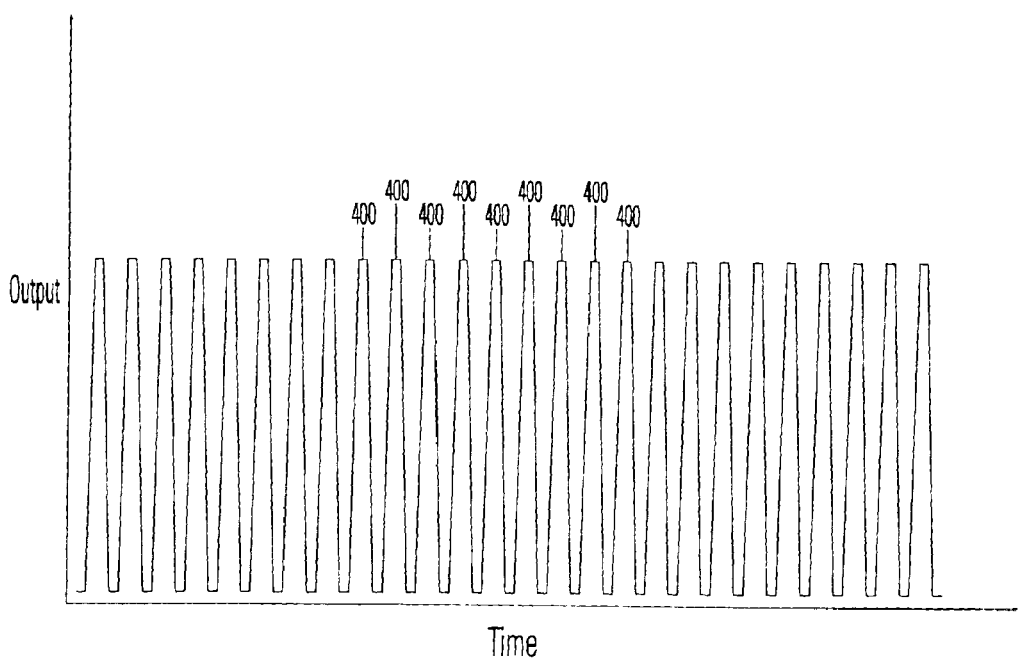
FIG. 4 depicts an exemplary output waveform of the FIG. 1 laser when the laser is operated in a quasi-CW mode.

In a third method embodiment of the invention, treatment of gynecological conditions is effected by operating laser 102 in a quasi-CW mode at an output power greater than 60 watts. The increased denaturization of the tissue is dramatic with increases in power, suggesting a threshold effect. As depicted in FIG. 4, laser 102 generates a continuous train of Q-switched micro-pulses 400 when operated in quasi-CW mode. The laser light is then delivered via optical fiber 106 to targeted tissue 104. Operation in a quasi-CW mode at powers above 60 watts facilitates formation of char and consequent rapid ablation rates, whereas operation in a quasi-CW mode at powers below 60 watts forms char more slowly and causes more thermal damage to underling tissue.

A fourth embodiment of this invention is to produce a high power, high beam quality laser that can project high power density laser light onto tissue. To do this the number of transverse optical modes supported by the resonator needs to be kept as low as possible.

Small $M^2$ and high average powers can be achieved by reducing the degree of thermal lensing in the laser element. Using laser diodes as the excitation source is one effective way of greatly reducing both the size of the lasing element and the thermal gradient responsible for creating the thermal lens. The reason for this is that while 2–10% of the light produced from a flashlamp or arc lamp is converted into useful laser light 30–60% of the light emitted from laser diodes can be converted to laser light. Since the energy that is not converted to laser light is converted into heat, laser diodes deposit significantly less heat in the lasing element and as a consequence create a less powerful thermal lens. In this manner laser diodes can be used to pump crystalline laser elements or fiber lasers to produce high beam quality lasers. Slab and waveguide lasers that can be pumped by laser diodes, arc lamps, or flashlamps are another method of creating low $M^2$ lasers. This is because the thermal gradient produced in slab lasers is linear across the thin dimension of the slab and not radially dependent in contrast to a typical cylindrical lasing element. The linear thermal gradient does not produce a thermal lens resulting in low $M^2$ values.

For example, as a result of the low $M^2$ some embodiments of this invention are capable producing laser light that upon exiting a flat end of a fiber having a diameter of 600 μm has a divergence of 15.3° or lower; 15° or lower; 10° or lower; or 5° or lower, and the power density can be 13,400 watts per $cm^2$, or greater.

Figure 5:
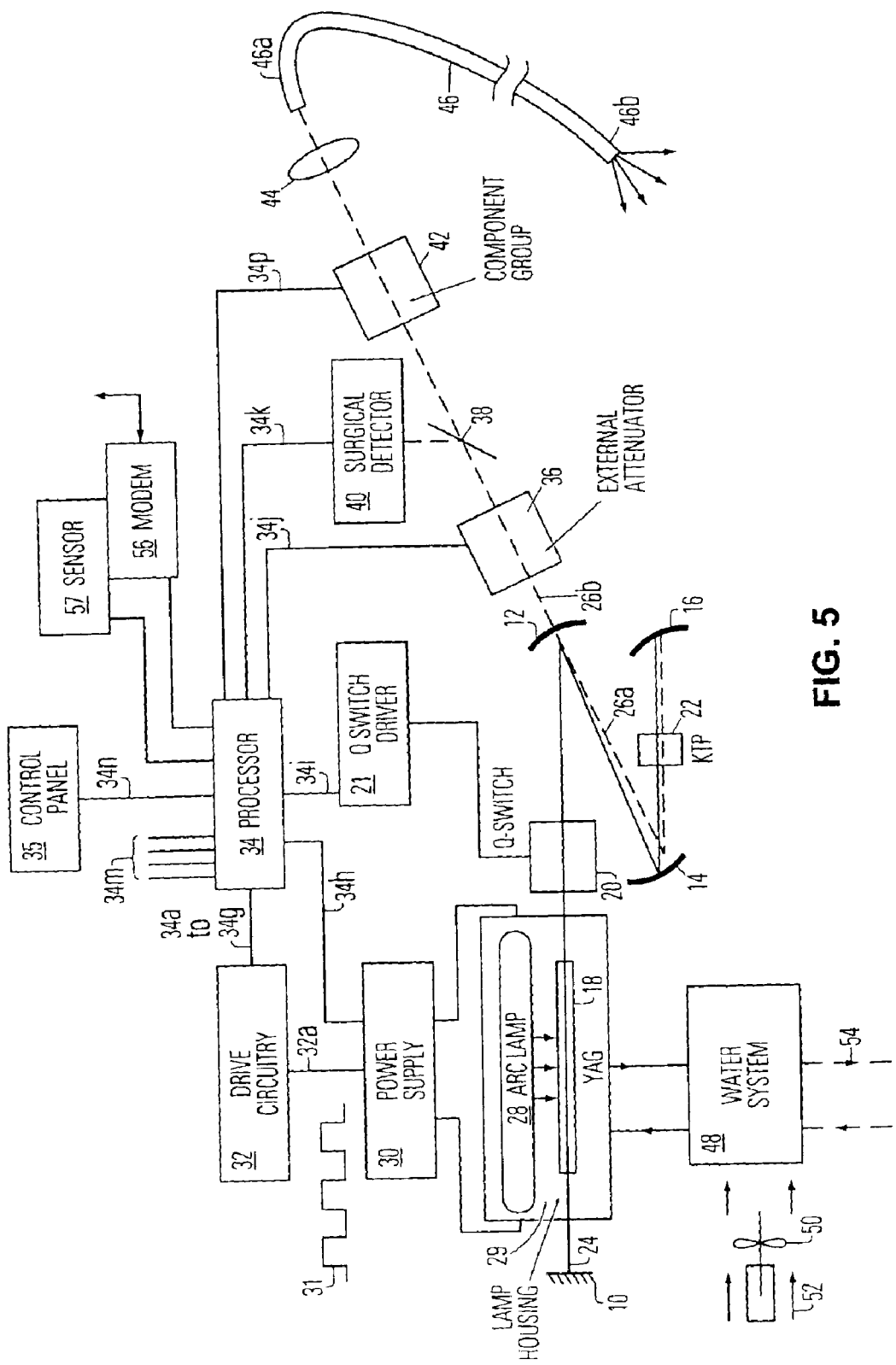
FIG. 5 is a block diagram of a laser system adaptable for use according to the present invention.

FIG. 5 shows a block diagram of a preferred laser system according to the present invention. In FIG. 5, a laser resonator is defined by end mirror 10, turning mirrors 12 and 14, and end mirror 16. All of these mirrors are high reflecting (greater than 99.8%) at the 1064 nm line. An optical path 24 is defined by these mirrors. A gain medium 18 comprising a Nd:YAG rod is mounted along the optical path within a pump housing 29. A laser diode array 28D is also mounted within the housing and supplies pump power to the gain medium in response to current generated in power supply 30. Representative laser diodes include laser diodes providing output in the range of 805 to 820 nm in wavelength with an input power to the array of pumping diodes in the range of 300 to 500 Watts. The laser diodes used for pump energy are operated in a modulated macro-pulse mode, or in a continuous mode, as suits a particular implementation.

Also in the optical path 24 is a Q-switch 20 between the lamp housing 29 and the turning mirror 12. A non-linear crystal 22 is mounted between the turning mirror 14 and the back mirror 16. This non-linear crystal is preferably a KTP crystal aligned for frequency doubling to generate a 532 nm beam. Mirrors 16 and 14 are highly reflective at 532 nm, while mirror 12 is transmissive and operates as an output coupler for the 532 nm beam.

Thus, the laser resonator is designed for resonating at a first frequency, i.e., 1064 nm along the Z-shaped optical path 24. A second frequency derived from the 1064 nm beam is generated in the KTP crystal 22. This beam travels along the path 26a and is extracted from the resonator to supply an output beam along path 26b.

The output beam along path 26b passes through a controllable attenuator 36, a beam splitter 38, which supplies a portion of the output beam to a surgical detector 40, and a component group 42 as described in more detail below. The attenuator, detector, and component group are all coupled to a data processing system 34, across lines 34j, 34k, and 34p.

The Q-switch 20 is controlled by Q-switch driver 21, which is, in turn, coupled to data processor 34 across line 34i. In the preferred system, the Q-switch is an acoustic-optic Q-switch.

Similarly, the power supply 30 generates an electrical power signal for controlling the diode array 28D. This power signal is controlled by the data processor 34 across line 34h and by drive circuitry 32 across line 32a. Drive circuitry 32a is controlled by the data processor across lines 34a through 34g. A sensor 57 is coupled with the data processor to sense an environmental condition, such as temperature or humidity, that affects operation of the laser system. A modem 56 is connected to the data processor 34, providing an interface for remote access to memory in the data processor. Finally, a control panel 35, by which a user can supply input signals and parameters, is provided. This control panel 35 is connected to the data processor 34 across line 34n.

In alternative systems, the non-linear crystal may be mounted outside the resonant cavity of the resonator. Also, it may be used for extracting outputs other than the second harmonic, such as sum-of-frequency derivation or the like.

The wavelength used according to the present invention for gynecological conditions treatment should be strongly absorbed in the tissue to help initiate and maintain tissue vaporization without creating deep tissue heating. The wavelength also must be minimally absorbed by the irrigant used during the procedure, typically physiologic saline solution. The 532 nm light produced by the system of FIG. 5, is both strongly absorbed in oxyhemoglobin and weakly absorbed in physiologic saline solution. Oxyhemoglobin is readily present in uterine tissue and serves as an efficient chromophore for 532 nm light. The differential in absorption coefficients between oxyhemoglobin and water at 532 nm is approximately 5 orders of magnitude ($10^5$). In other embodiments, wavelengths in the range from 200 nm–650 nm are used, which have strong oxyhemoglobin absorption and relatively weak water absorption (>$10^2$X). In yet other embodiments, wavelengths in the range from 200 nm to 650 nm range are used, which have strong oxyhemoglobin absorption and relatively weak water absorption (>10X).

Figure 6:
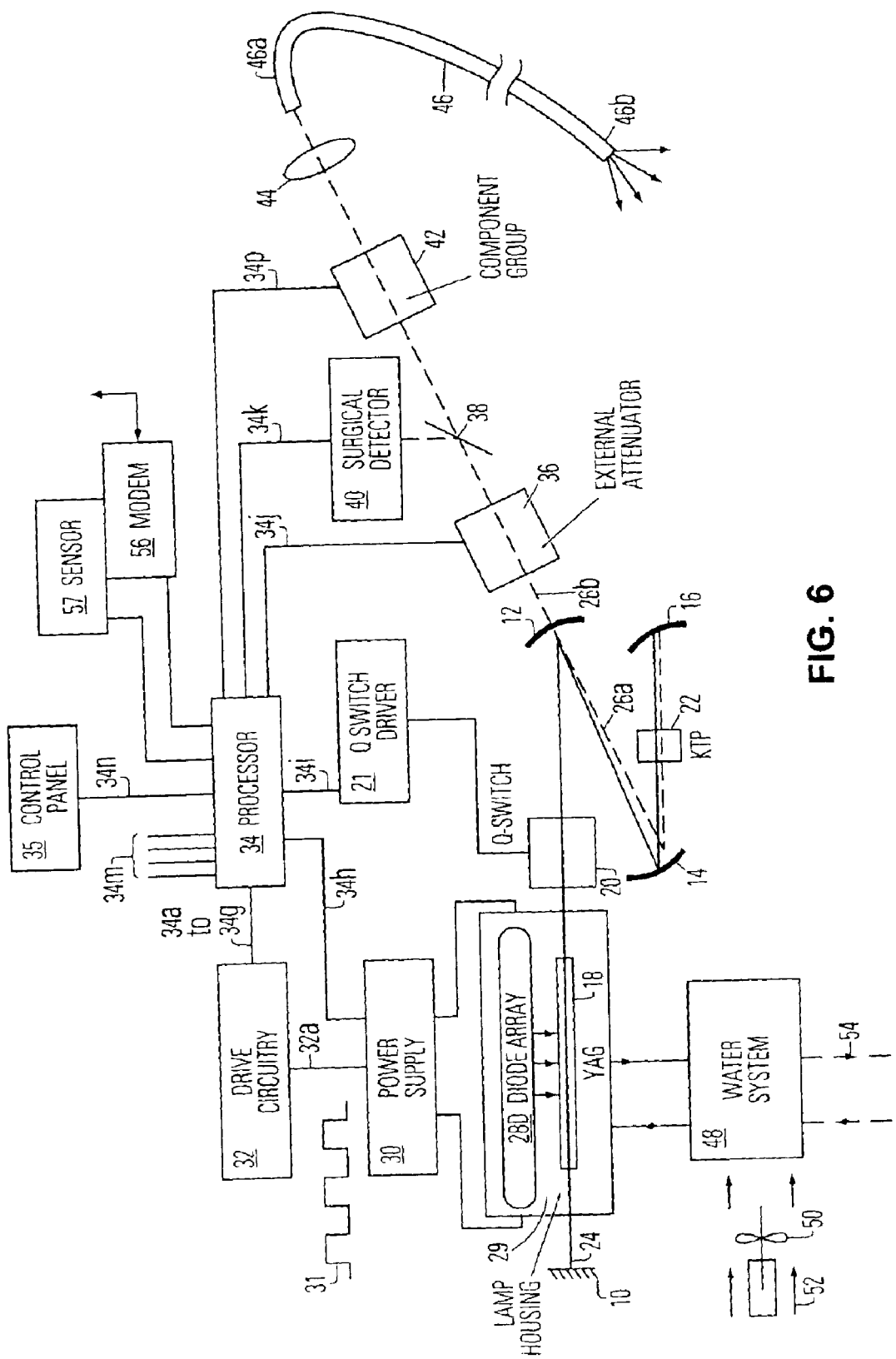
FIG. 6 is a block diagram of an alternative laser system adaptable for use according to the present invention.

Of course, as shown in FIG. 6, in which like components have the same reference numerals as in FIG. 5, alternative pump power sources, such as arc lamps 28, and flash lamps, other lasers for longitudinal pumping, and others, can be used as suits the needs of a particular gain medium and application of the laser system.

The laser systems shown in FIGS. 5 and 6 can be modified by removing both the Q-switch and the external surgical attenuator. The Q-switch and surgical attenuator are removed because the modulated pump power provides a great deal of flexibility in controlling the output power of the laser not attainable using a Q-switch. The data processing system can be programmed to maintain a constant thermal load in the laser system while varying the peak pump power widely. Thus, the peak current and duty cycle of the pump power source can be adjusted in such a way to keep the average pump power constant, but the second harmonic power during the ready and work modes adjusted by selecting the peak current and duty cycle. Although it may be necessary to use attenuators in the beamline during the ready mode in order to extract an aim beam, such attenuators may well be eliminated for the work mode. The average power does not have to be constant, rather it can be maintained at levels which keep thermal focusing of the gain medium within the range of stability of the resonator.

A representative laser system adapted for delivery of energy as described above, comprises an 80 watt average power, 532 nm output wavelength, solid state, intra-cavity frequency doubled Nd:YAG laser. To obtain optimal efficiency, an arc lamp pump source is modulated at a period of 4.5 ms with a 16 ms duty cycle, generating 285 watts peak macro-pulse power. An intra-cavity acousto-optic AO Q-switch is used to further modulate the energy at a period of 40 kHz with a 450 us micro-pulse. The laser energy is coupled to a side firing fiber optic delivery device for delivery to uterine tissue.

The laser system uses a combination touch screen and control knob user interface to assist the operator in setting up the surgical parameters, including power levels and pulse sequence specifications. The average power setting is prominently displayed on the screen. Parameter adjustments are made by first activating (touching) the desired parameter box on the screen and then turning the knob. The laser system uses a secure card key interface to enable the laser. The system is transportable. The system offers convenient storage and a fiber delivery device pole.

Figure 7:
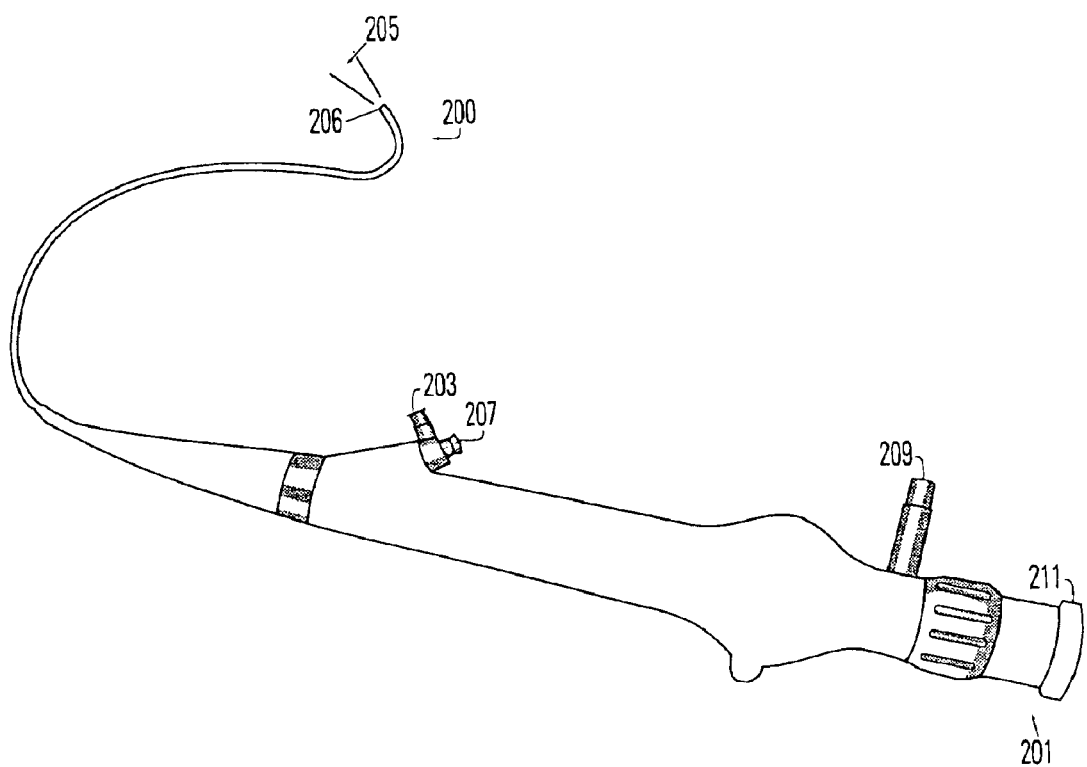
FIG. 7 is a diagram of a flexible tip hysteroscope, adaptable for use according to the present invention.

An example of an endoscope, in particular a hysteroscope, for use with the present invention is shown in FIG. 7. The hysteroscope has a distal end 200 and a proximal end 201. Laser radiation 205 is directed from and end firing fiber through an opening 206, by a fiber optic component. Water, Ringer Lactate or saline solution is delivered and removed from the treatment area via lumens in the probe. A viewing optic is also placed in the opening 206, by which the surgeon is able to view the treatment area during the procedure. On the proximal end 201 of the endoscope, an irrigation port 203 for flow of the irrigant is provided. Also, a fiber port 207 is used for insertion and removal of the fiber optic delivering laser radiation to the treatment area. A light source connector 209 is used for supplying light to the treatment area for visualization. An viewing port 211, which can be coupled to a video camera, or looked into directly, is also included on the representative hysteroscope. The endoscope includes a flexible tip in one embodiment, and controls (not shown) in the near proximal end 201, by which the surgeon deflects and guides the positioning of the tip at distal end 200. Representative systems for providing flexible tip endoscopes are described in U.S. Pat. No. 4,802,461, and are widely used for surgical procedures.

The vaporization of uterine tissue using oxyhemoglobin as the primary chromophore is related to the incident power density, or irradiance, which can be expressed in Watts/cm$^2$. The overall rate of uterine tissue vaporization is a function of the spot size, absorption depth, and the power density. A large spot with high power density, and rapid absorption is ideal to rapidly vaporize tissue. A high power light source is required to achieve a large spot, high power density treatment beam. Peak laser power, average laser power, beam quality, delivery device design and delivery device placement all affect the efficiency of vaporization. A treatment beam 28.5 Kw/cm$^2$ average irradiance with a 85.5 Kw/cm$^2$ peak irradiance macro-pulse, with a spot size between about 0.2 and 0.5 mm$^2$, rapidly vaporizes tissue.

FIGS. 8 and 9 illustrate the different optical penetration depths of the 532 nm wavelength and 1064 nm wavelength used in prior art procedures. See, S. L. Jacques. *Laser-tissue interaction. Photochemical, photothermal, and photomechanical*. Surg. Clin N. Am. 1992;72(3):531–558. The optical penetration depth of the 1064 wavelength beam from Nd:YAG laser beam is about 10 mm, which is 13 times larger than the penetration depth of the second harmonic 532 wavelength laser beam, which is about 0.8 mm. As a result, the 1064 laser power is spread out over a much larger tissue volume than the power of the KTP laser. In case of the 1064 laser as shown in FIG. 9, the temperature at the tissue surface barely reaches 100° C. Therefore, only a small portion of tissue gets vaporized. But a huge volume of tissue gets coagulated (see space between 100° C. and 60° C. isotherm).

The 532 laser beam, in contrast, is substantially completely absorbed within less than about 1 mm of the surface of uterine tissue. The laser power is confined to a very small tissue volume. The high volumetric power density results in a fast heating of the tissue and efficient tissue vaporization. Volumetric power density delivered to tissue is a function of the absorbtion depth, irradiance in Watts/cm$^2$ and spot size on the surface of the tissue. The coagulation zone is very thin because of the small optical penetration depth of the 532 wavelength, and because substantially all of the radiation is converted to vaporization rather than residual heat.

Other wavelengths which are substantially completely absorbed within less than about 1 mm of the surface of the uterine tissue include wavelengths between about 200 and 1000 nm, including wavelengths less than about 700 nm, for example between about 200 nm and 650 nm.

FIGS. 10 and 11 illustrate a profile of a beam delivered to tissue using one representative side firing optical fiber, to show spot size as a function of distance from the side of the optical fiber. FIG. 10 is an end view, showing a fiber 600, cladding 601 on the fiber, an air space 602, and a tip 603 through which the beam is directed by a reflecting face on the fiber. The cross-section of the beam is represented by the crossing lines 604 and 605. As shown, the beam has a width in this dimension of about 0.35 mm at 1 mm from the side of the tip 603. At about 2 mm from the side of the tip 603, the width is about 1 mm. At about 3 mm distance from the side of the tip 603, the beam width is about 2.2 mm.

FIG. 11 is a side view, with like components given the same reference numbers. The beam width in this dimension is represented by lines 606 and 607. As shown, the beam has a width in this dimension of about 0.7 mm at 1 mm from the side of the tip 603. At about 2 mm from the side of the tip 603, the width is about 1 mm. At about 3 mm distance from the side of the tip 603, the beam width is about 1.5 mm.

Thus, the spot size at 1 mm from the side of the tip is defined basically by an ellipse having a major axis of 0.7 mm, and a minor axis of 0.35 mm. The area of the spot at 1 mm is around 0.2 mm$^2$. At 2 mm from the side, the area of the spot is about 0.8 mm$^2$.

For rapid procedures, according to the present invention, the spot size should be large enough that the operator can remove tissue at a reasonable rate, and see the results of a single pass of the spot over a region of tissue. If the spot size is too small, the rate of the operation is too slow. Also, if the spot size is too big, then the procedure is difficult to control precisely. A preferred spot size is less than about 1 mm$^2$, and more particularly between about 0.8 mm$^2$ and about 0.05 mm$^2$. Other apparatus may be used for delivery of the beam with the desired spot size, including embodiments without diverging beams, and embodiments with converging beams.

The irradiance of the beam at 1 mm from the side of the tip for an 80W average power laser as described above is about 30 kiloWatts/cm$^2$. According to the present invention, it is desirable to provide a wavelength between about 650 and 200 nm, with a spot size on the surface of the tissue less than about 0.8 mm$^2$, and preferably greater than about 0.05 mm$^2$, with an irradiance greater than about 10 kiloWatts/cm$^2$, and more preferably greater than 20 kiloWatts/cm$^2$, and even more preferably 30 kiloWatts/cm$^2$ or higher.

Figure 12:
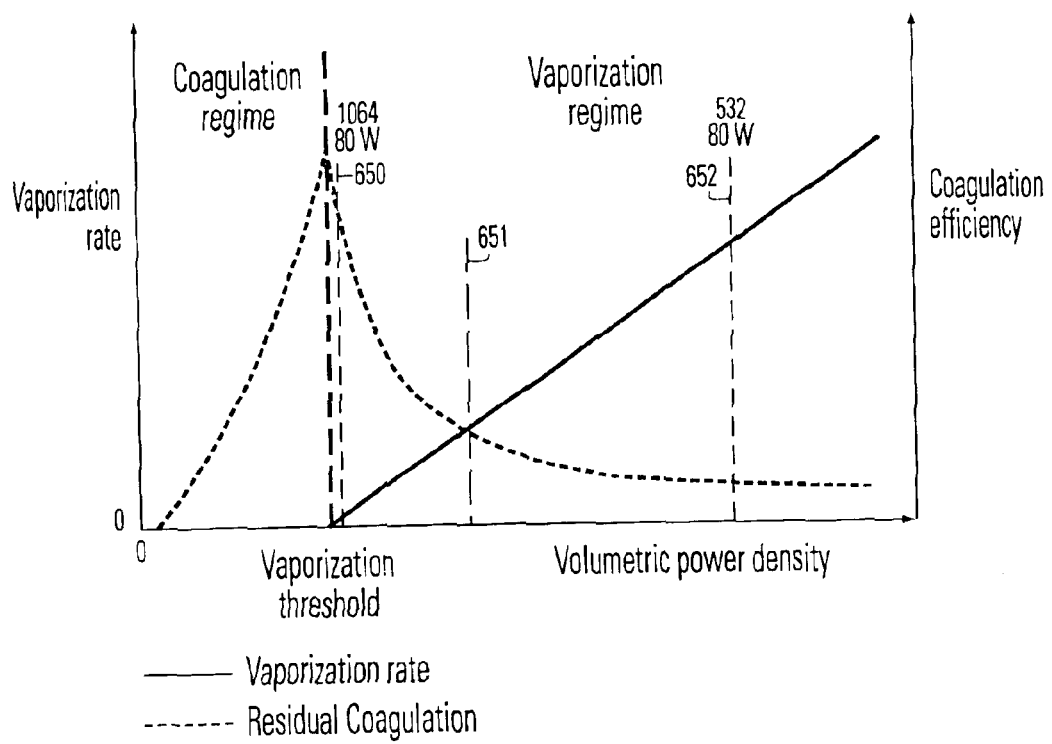
FIG. 12 is a heuristic diagram illustrating operation of the present invention.

FIG. 12 shows, heuristically, how vaporization rate and coagulation rate depend on the volumetric power density. The vaporization rate (in mm/s) is defined as tissue depth that is vaporized per time interval. The coagulation rate (in mm/s) is defined as the depth of residual coagulated tissue that remains after a certain time of vaporization.

Below a certain volumetric power density, referred to as a "vaporization threshold" in FIG. 12, no tissue gets vaporized. All laser energy stays inside the tissue. Tissue coagulation occurs where the tissue temperature rises above approximately 60° C. As the volumetric power density is increased a bigger and bigger tissue volume gets coagulated.

At the vaporization threshold, vaporization starts. Above the vaporization threshold the vaporization rate can be considered to increase linearly with the volumetric power density for the purpose of understanding the present invention, and as described by a steady state model for continuous wave laser tissue ablation, known by those familiar with the art of laser-tissue interaction.

As more and more laser energy is consumed by vaporization of the tissue, the amount of laser energy leading to residual tissue coagulation gets smaller, i.e. the amount of residual coagulation drops. Thus, extent of the zone of thermal damage characterized by tissue coagulation left after the procedure gets smaller with increasing volumetric power density, while the rate of vaporization increases. Substantial and surprising improvement in results is achieved.

Publications about visual laser ablation of the prostate (VLAP) that is performed with an Nd:YAG laser at 1064 nm have shown that this type of laser is not able to vaporize a significant amount of tissue. Histology studies have shown that the 1064 nm laser induces deep coagulation in the tissue that results in edema and delayed tissue sloughing. This effect was described by Kuntzman, et al., *High-power potassium titanyl phosphate laser vaporization prostatectomy*.

Mayo Clin Proc 1998:73:798–801. Thus, in the heuristic diagram of FIG. 12, the VLAP procedure is believed to lie around point 650, barely above the vaporization threshold. Also, prior art technologies using 532 nm with spot sizes on the order of 1 mm² with average output power of 60 Watts, are believed to lie, heuristically, around point 651 in the FIG. 12. Kuntzman et al present results for the coagulation depth of a 60 W continuous wave 532 nm laser, with suggested operation at a distance of 2 mm from the side of the tip, yielding less than 5 kiloWatts/cm² irradiance.

As the laser power is further increased to 80 W, and the side firing probe is placed less than 1 mm from the tissue for a small spot size, the ablation rate further increases and the coagulation rate further drops, so that the procedure lies heuristically at point 652 in FIG. 12.

A 80 Watt KTP laser can be used to easily reach irradiance levels that vaporize substantially more tissue than is left as residual coagulation after the procedure. More precisely, the vaporization rate is substantially higher than the coagulation rate as given by the definition above, using high irradiance levels that are easily achieved with higher power lasers. Because of higher vascularization in the uterus, the optical penetration depth is lower than in prostatic tissue, and therefore the volumetric power density at the vaporization threshold can be easily reached with lower average power lasers, including for example a 40 W average output power laser.

Figure 13:
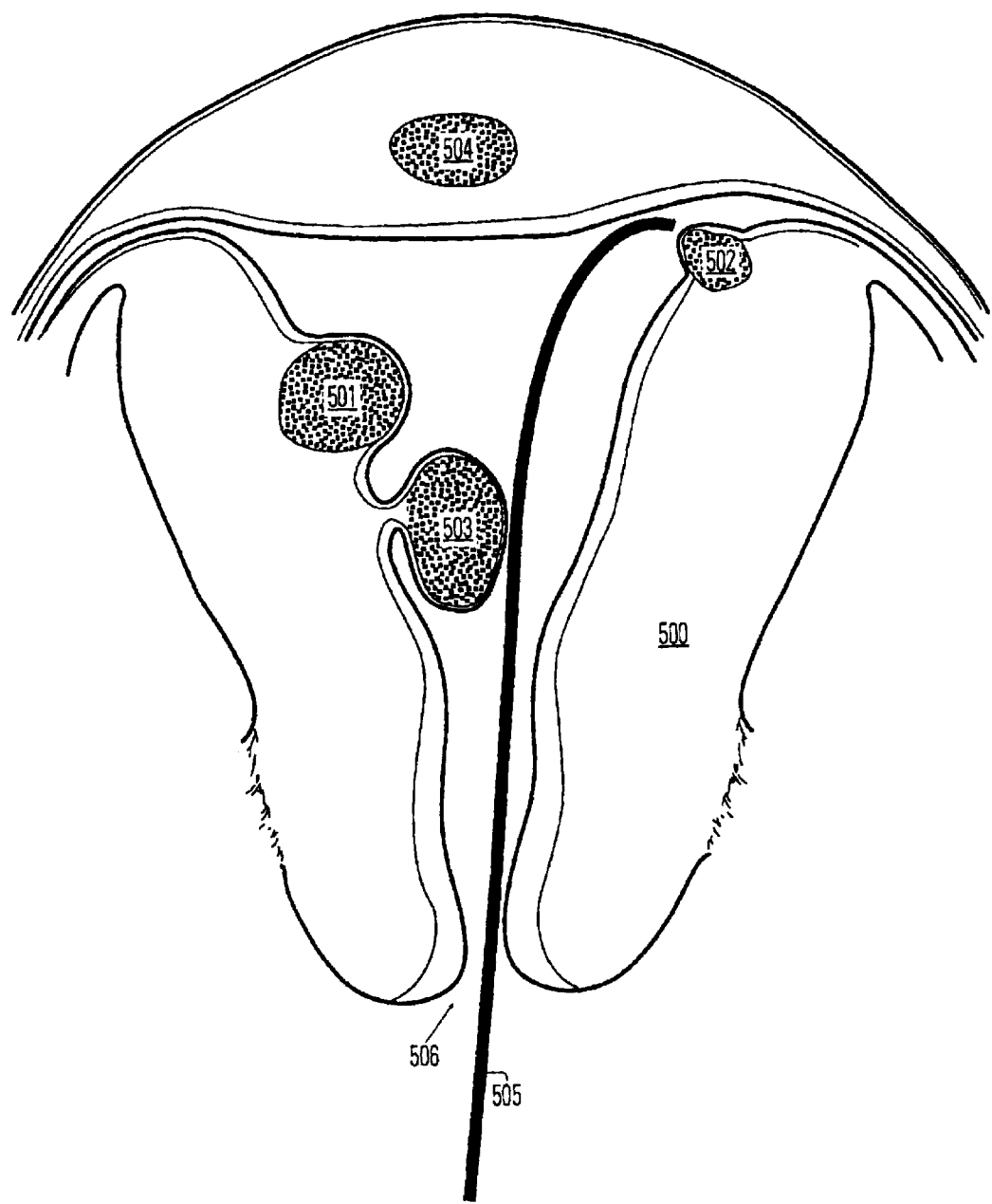
FIG. 13 illustrates representative gynecological conditions treatable according to the present invention.

FIG. 13 illustrates a uterus, generally 500, having myomas treatable according to the present invention, including intracavitery protruding myomas 501, 502, intracavitery pedunculated myoma 503, and intramural, submucosal myoma 540. Myoma 502 is located in the right cornu. Hysteroscope 505 is positioned through the cervix 506 with a flexible tip 507 adjacent myoma 502, and delivering laser radiation as described above.

Figure 14:
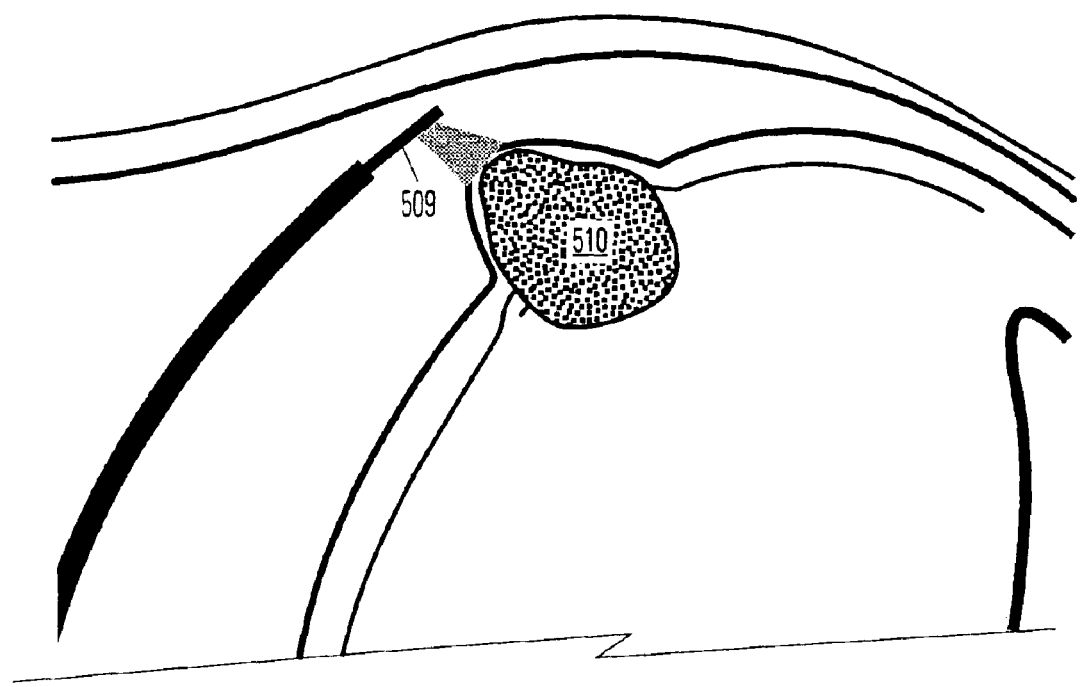
FIG. 14 illustrates application of a side-firing probe on a hysteroscope for ablation of tissue in treatment of a protruding, intracavitery uterine myoma within the right uterine cornu.
Figure 15:
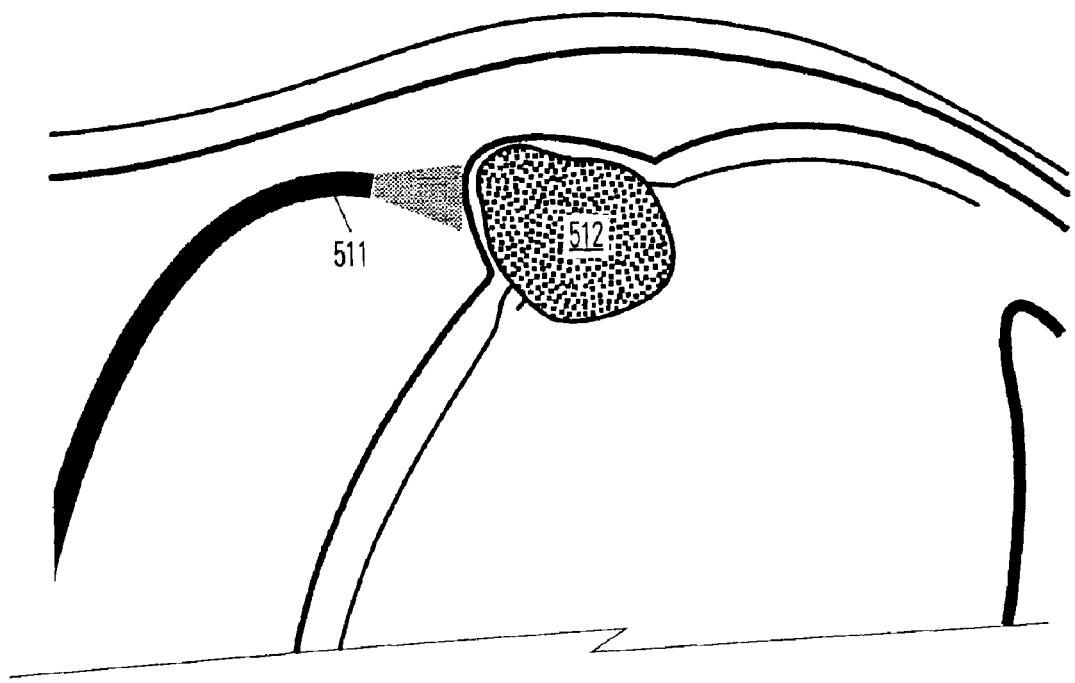
FIG. 15 illustrates application of an end-firing probe on a flexible tip hysteroscope for ablation of tissue in treatment of a protruding, intracavitery uterine myoma.

FIG. 14 illustrates use of a side firing probe 509 for treatment of a myoma 510 located in one of the uterine cornua. FIG. 15 illustrates use of an end firing probe 511, for treatment of a myoma 512 located in one of the uterine cornua.

While the invention has been particularly shown and described with reference to preferred embodiments thereof, it will be understood by those skilled in the art, that various changes in form and details may be made therein without departing from the spirit and scope of the invention, as defined by the appended claims.

What is claimed is:

1. A method for photoselective vaporization of tissue for treatment of gynecological conditions, comprising:
   delivering laser radiation to a treatment area on a surface of tissue of a female reproductive organ, the laser radiation being absorbed substantially completely by the tissue within about 1 mm of the surface, and having average irradiance in the treatment area greater than 10 kiloWatts/cm² in a spot size at least about 0.05 mm²; wherein said delivering comprises using a hysteroscope, with one of an optical fiber having a side firing optical element and an end firing optical fiber adapted for directing laser radiation from the fiber to the treatment area, and placing said side firing optical element or end firing optical fiber within about 1 mm, or less, of the treatment area.

2. The method of claim 1, wherein the spot size is between about 0.1 and 0.8 mm² in the treatment area.

3. The method of claim 1, wherein the irradiance is at least 30 kiloWatts/cm² in the treatment area.

4. The method of claim 1, wherein the laser radiation has a wavelength in a range from about 200 to about 700 nm.

5. The method of claim 1, wherein the delivered laser radiation has a wavelength in a range of about 200 nm to about 700 nm, and has an average irradiance in the treatment area greater than 20 kiloWatts/cm².

6. The method of claim 1, wherein the delivered laser radiation has a wavelength in a range of about 200 nm to about 700 nm, and has an average irradiance in the treatment area greater than 30 kiloWatts/cm².

7. The method of claim 1, wherein said tissue comprises uterine tissue.

8. The method of claim 1, wherein said tissue comprises uterine tissue located in a cornua of the uterus.

9. The method of claim 1, wherein said delivering comprises using a hysteroscope, with an optical fiber adapted to direct laser radiation from the fiber to the treatment area.

10. The method of claim 1, wherein said delivering comprises using a hysteroscope, with an end firing optical fiber.

11. The method of claim 1, including generating said laser radiation using a solid state laser with greater than 40 Watts average output power.

12. The method of claim 1, including generating said laser radiation using a solid state laser with greater than 60 Watts average output power.

13. The method of claim 1, including generating laser radiation using a macro-pulsed solid state laser having output power greater than about 200 Watts during a macro-pulse.

14. The method of claim 1, wherein said delivering comprises delivering a macro-pulse consisting of a sequence of micro-pulses of laser radiation, and said irradiance is greater than 50 kiloWatts/cm² during the macro-pulse.

15. The method of claim 1, including generating said laser radiation using Neodymium doped solid state laser medium, and optics to produce an output at a second or higher harmonic frequency with greater than 40 Watts average output power.

16. The method of claim 1, wherein said tissue comprises uterine tissue, and said treatment is for a gynecological condition selected from leiomyoma uteri, rhabdomyoma, endometriosis, endometrial hyperplasia, endometrial cysts, endometrial polyps, menorrhagia, uterine septa, intrauterine adhesions, or cervical intraepithelial neoplasia.

17. A method for photoselective vaporization of tissue for treatment of gynecological conditions, comprising:
   delivering laser radiation to a treatment area on a surface of tissue of a female reproductive organ, the laser radiation being absorbed substantially completely by the tissue within about 1 mm of the surface, and having average irradiance in the treatment area greater than 10 kiloWatts/cm² in a spot size at least about 0.05 mm², wherein the laser radiation has a beam quality ($M^2$) that is less than or equal to 100.

18. The method of claim 17, wherein said delivering comprises using a hysteroscope, with an optical fiber adapted to direct laser radiation from the fiber to the treatment area.

19. A method for photoselective vaporization of tissue of a female reproductive organ, comprising:
   delivering laser radiation and a flow of a transparent liquid irrigant to a treatment area on a surface of target tissue of a female reproductive organ, the laser radiation causing vaporization of a volume of tissue greater than a volume of residual coagulation of tissue, and having irradiance in the treatment area greater than 10 kiloWatts/cm² in a spot size at least 0.05 mm²; wherein said delivering comprises using a hysteroscope, with one of an optical fiber having a side firing optical element and an end firing optical fiber adapted for directing laser radiation from the fiber to the treatment area, ad placing said side firing optical element or end firing optical fiber within about 1 mm, or less, or the treatment area.

20. The method of claim 19, wherein the spot size is less than about 0.8 mm$^2$ in the treatment area.

21. The method of claim 19, wherein the irradiance is at least 30 kiloWatts/cm$^2$ in the treatment area.

22. The method of claim 19, wherein the laser radiation has a wavelength in a range from about 200 to about 700 nm.

23. The method of claim 19, wherein the delivered laser radiation has a wavelength in a range of about 200 nm to about 700 nm, and has an average irradiance in the treatment area greater than 20 kiloWatts/cm$^2$.

24. The method of claim 19, wherein the delivered laser radiation has a wavelength in a range of about 200 nm to about 700 nm, and has an average irradiance in the treatment area greater than 30 kiloWatts/cm$^2$.

25. The method of claim 19, wherein the irrigant comprises physiologic saline.

26. The method of claim 19, wherein said delivering comprises using a hysteroscope with a flexible tip.

27. The method of claim 19, wherein said delivering comprises using a hysteroscope, with an optical fiber having a side firing optical element.

28. The method of claim 19 wherein said delivering comprises using a hysteroscope, with an end firing optical fiber.

29. The method of claim 19, including generating said laser radiation using a solid state laser with greater than 40 Watts average output power.

30. The method of claim 19, including generating said laser radiation using a solid state laser with greater than 60 Watts average output power.

31. The method of claim 19, including generating laser radiation using a macro-pulsed solid state laser having output power greater than about 200 Watts during a macro-pulse.

32. The method of claim 19, wherein said delivering comprises delivering a macro-pulse consisting of a sequence of micro-pulses of laser radiation, and said irradiance is greater than 50 kiloWatts/cm$^2$ during a macro-pulse.

33. The method of claim 19, including generating said laser radiation using Neodymium doped solid state laser medium, and optics to produce an output at a second or higher harmonic frequency with greater than 40 Watts average output power.

34. The method of claim 19, wherein said target tissue comprises uterine tissue, and said treatment is for a gynecological condition selected from leiomyoma uteri, rhabdomyoma, endometriosis, endometrial hyperplasia, endometrial cysts, endometrial polyps, menorrhagia, uterine septa, intrauterine adhesions, or cervical intraepithelial neoplasia.

35. A method for photoselective vaporization of tissue of a female reproductive organ, comprising:
delivering laser radiation and a flow of a transparent liquid irrigant to a treatment area on a surface of a target tissue of a female reproductive organ, the laser radiation causing vaporization of a volume of tissue greater than a volume of residual coagulation of tissue, and having irradiance in the treatment area greater than 10 kioWatts/cm$^2$ in a spot size at least 0.05 mm$^2$, wherein the irrigant comprises Ringer's Lactate.

36. The method of claim 35, wherein said delivering comprises using a hysteroscope, with an optical fiber adapted to direct laser radiation from the fiber to the treatment area.

37. A method for photoselective vaporization of tissue of a female reproductive organ, comprising:
delivering laser radiation and a flow of a transparent liquid irrigant to a treatment area on a surface of target tissue of a female reproductive organ, the laser radiation causing vaporization of a volume of tissue greater than a volume of residual coagulation of tissue, and having irradiance in the treatment area greater than 10 kiloWatts/cm$^2$ in a spot size at least 0.05 mm$^2$, wherein the laser radiation has a beam quality ($M^2$) that is less than or equal to 100.

38. The method of claim 1, 17, 19, 35, 37, wherein the laser radiation has a wavelength of about 532 nm.

39. A method for photoselective vaporization of tissue for treatment of a gynecological condition, comprising:
delivering laser radiation to a treatment area on tissue of a female reproductive organ, the laser radiation having a wavelength and having irradiance in the treatment area sufficient to cause vaporization of a substantially greater volume of said tissue than a volume of residual coagulated tissue caused by the laser radiation; wherein said delivering comprises using a hysteroscope, with one of an optical fiber having a side firing optical element and an end firing optical fiber adapted for directing laser radiation from the fiber to the treatment area, and placing said side firing optical element or end firing optical fiber within about 1 mm, or less, of the treatment area.

40. The method of claim 39, wherein the delivered laser radiation has an average irradiance in the treatment area greater than 10 kiloWatts/cm$^2$ in a spot size at least 0.05 mm$^2$.

41. The method of claim 39, including delivering said laser radiation using an optical fiber, and wherein the delivered laser radiation has a wavelength in a range of about 200 nm to about 650 nm, and has an average irradiance in the treatment area greater than 10 kiloWatts/cm$^2$ and the optical fiber is adapted to cause a spot size of at least about 0.05 mm$^2$ in the treatment area.

42. The method of claim 39, wherein the delivered laser radiation has a wavelength in a range of about 200 nm to about 650 nm, and has an average irradiance in the treatment area greater than 20 kiloWatts/cm$^2$ and the optical fiber is adapted to cause a spot size of at least about 0.05 mm$^2$ in the treatment area.

43. The method of claim 39, wherein the delivered laser radiation has a wavelength in a range of about 200 nm to about 650 nm, and has an average irradiance in the treatment area greater than 30 kiloWatts/cm$^2$ and the optical fiber is adapted to cause a spot size of at least about 0.05 mm$^2$ in the treatment area.

44. The method of claim 39, wherein the spot size is less than about 0.8 mm$^2$ in the treatment area.

45. The method of claim 39, wherein the average irradiance is at least 30 kiloWatts/cm$^2$ in the treatment area.

46. The method of claim 39, wherein the laser radiation has a wavelength in a range from about 200 to about 700 nm.

47. The method of claim 39, including delivering a flow of irrigant to the treatment area.

48. The method of claim 39, wherein the tissue comprises uterine tissue.

49. The method of claim 39, wherein said delivering comprises using a hysteroscope, with an optical fiber having a side firing optical element.

50. The method of claim 39, wherein said delivering comprises using a hysteroscope, with an end firing optical fiber.

51. The method of claim 39, including generating said laser radiation using a solid state laser with greater than 40 Watts average output power.

52. The method of claim 39, including generating said laser radiation using a solid state laser with greater than 60 Watts average output power.

53. The method of claim 39, including generating laser radiation using a macro-pulsed solid state laser having output power greater than about 200 Watts during a macro-pulse.

54. The method of claim 39, wherein said delivering comprises delivering a macro-pulse consisting of a sequence of micro-pulses of laser radiation, and said irradiance is greater than 50 kiloWatts/cm$^2$ during the macro-pulse.

55. The method of claim 39, including generating said laser radiation using Neodymium doped solid state laser medium, and optics to produce an output at a second or higher harmonic frequency with greater than 40 Watts average output power.

56. The method of claim 39, including generating said laser radiation using a diode-pumped, Neodymium doped solid state laser medium, and optics to produce an output at a second or higher harmonic frequency with greater than 40 Watts average output power.

57. The method of claim 39, wherein said tissue comprises uterine tissue, and said treatment is for a gynecological condition selected from leiomyoma uteri, rhabdomyoma, endometriosis, endometrial hyperplasia, endometrial cysts, endometrial polyps, menorrhagia, uterine septa, intrauterine adhesions, or cervical intraepithelial neoplasia.

58. A method for photoselective vaporization of tissue for treatment of a gynecological condition, comprising:
  delivering laser radiation to a treatment area on tissue of a female reproductive organ, the laser radiation having a wavelength and having irradiance in the treatment area sufficient to cause vaporization of a substantially greater volume of said tissue than a volume of residual coagulated tissue caused by laser radiation, wherein the laser radiation has a beam quality (M$^2$) that is less than or equal to 100.

59. The method of claim 58, wherein said delivering comprises using a hysteroscope, with an optical fiber adapted to direct laser radiation from the fiber to the treatment area.

60. A method for photoselective vaporization of gynecological tissue, comprising:
  generating laser radiation using a Neodymium doped solid state laser medium, and optics producing a second or higher harmonic output with greater than 40 Watts average output power;
  coupling said output to an optical fiber in an endoscope having a flexible tip, the optical fiber adapted to direct laser radiation from the fiber to a treatment area on a surface of the tissue;
  delivering a flow of irrigant to the treatment area; and
  delivering laser radiation to a treatment area on the tissue via the optical fiber, the laser radiation having a wavelength and having irradiance in the treatment area sufficient to cause vaporization of a substantially greater volume of tissue than a volume of residual coagulated tissue caused by the laser radiation; wherein the optical fiber includes one of a side firing tip and an end firing tip, and including placing said one of a side firing tip and an end firing tip within about 1 mm, or less, of the treatment area.

61. The method of claim 60, wherein said average output power is greater than 60 watts.

62. The method of claim 60, wherein the delivered laser radiation has an average irradiance in the treatment area greater than 10 kiloWatts/cm$^2$ and the optical fiber is adapted to cause a spot size of at least about 0.05 mm$^2$ in the treatment area.

63. The method of claim 60, wherein the delivered laser radiation has an average irradiance in the treatment area greater than 20 kiloWatts/cm$^2$ and the optical fiber is adapted to cause a spot size of at least about 0.05 mm$^2$ in the treatment area.

64. The method of claim 60, wherein the delivered laser radiation has an average irradiance in the treatment area greater than 30 kiloWatts/cm$^2$ and the optical fiber is adapted to cause a spot size of at least about 0.05 mm$^2$ in the treatment area.

65. The method of claim 60, wherein the delivered laser radiation has an average irradiance in the treatment area greater than 10 kiloWatts/cm$^2$, and the optical fiber is adapted to cause a spot size is less than about 0.8 mm$^2$ in the treatment area.

66. The method of claim 60, wherein the average irradiance is at least 30 kiloWatts/cm$^2$ in the treatment area.

67. The method of claim 60, wherein the optical fiber includes a side firing tip.

68. The method of claim 60, wherein the optical fiber includes an end firing tip.

69. The method of claim 60, including Q-switching said laser medium to produce micro-pulses during application of input power to the laser medium, and applying input power to the laser medium in a sequence of pulses to generate macro-pulses of output radiation, and wherein said output power is greater than about 200 Watts during said macro-pulses.

70. The method of claim 60, including Q-switching said laser medium to produce micro-pulses during application of input power to the laser medium, and applying input power to the laser medium in a sequence of pulses to generate macro-pulses of output radiation, and said irradiance is greater than 50 kiloWatts/cm$^2$ during the macro-pulse.

71. The method of claim 60, wherein said tissue comprises uterine tissue, and said treatment is for a gynecological condition selected from leiomyoma uteri, rhabdomyoma, endometriosis, endometrial hyperplasia, endometrial cysts, endometrial polyps, menorrhagia, uterine septa, intrauterine adhesions, or cervical intraepithelial neoplasia.

72. A method for photoselective vaporization of gynecological tissue, comprising:
  generating laser radiation using a Neodymium doped solid state laser medium, and optics producing a second or higher harmonic output with greater than 40 Watts average output power;
  coupling said output to an optical to an optical fiber in an endoscope having a flexible tip, the optical fiber adapted to direct laser radiation from the fiber to a treatment area on a surface of the tissue;
  delivering a flow of irrigant to the treatment area; and
  delivering laser radiation to a treatment area on the tissue via the optical fiber, the laser radiation having a wavelength and having irradiance in the treatment area sufficient to cause vaporization of a substantially greater volume of tissue than a volume of residual coagulated tissue caused by the laser radiation, wherein the laser radiation has a beam quality (M$^2$) that is less than or equal to 100.

73. A method for treating gynecological conditions, comprising:
  providing a solid-state laser emitting light with a wavelength of 200 to 1000 nm having a laser element positioned to receive pump radiation from a pump radiation source;

modulating the pump radiation source to cause the laser element to emit laser light having pulse duration between 0.1 and 500 milliseconds and pulse frequencies between 1 and 500 Hz; and delivering the laser light to targeted tissue of a female reproductive organ; wherein the laser radiation has a beam quality ($M^2$) that is less than or equal to 100.

74. The method of claim 73, wherein the light is of a wavelength that is better absorbed by the targeted tissue than by a substance in an intermediate position between the tissue and a device used to deliver the laser light to the tissue.

75. The method of claim 73, wherein the output power density of the light delivered to the targeted tissue is high enough to vaporize the tissue.

76. The method of claim 73, wherein the laser light has a repetition rate of between 1 Hertz and 500 Hertz.

77. The method of claim 73, wherein said delivering includes using an optical fiber which terminates in an end-firing probe emitting the laser light from an end of the optical fiber.

78. The method of claim 73, wherein said delivering includes using an optical fiber that terminates in a side-firing probe emitting the laser light in a direction transverse to the longitudinal axis of the optical fiber.

79. The method of claim 73, wherein the laser further comprises a frequency doubling element.

80. The method of claim 73, wherein the step of delivering the laser light further comprises transmitting the laser light through an optical fiber.

81. The method of claim 73, wherein the laser element is fabricated from neodymium doped YAG (Nd:YAG).

82. The method of claim 73, further comprising the step of Q-switching the laser to produce a train of micropulses, each micropulse train collectively form a pulse.

83. The method of claim 73, wherein the pump radiation source is a laser diode.

84. The method of claim 73, wherein the pump radiation source is an arc lamp.

85. The method of claim 73, wherein the pump radiation source is a flash lamp.

86. The method of claim 73, wherein said tissue comprises uterine tissue, and said treatment is for a gynecological condition selected from leiomyoma uteri, rhabdomyoma, endometriosis, endometrial hyperplasia, endometrial cysts, endometrial polyps, menorrhagia, uterine septa, intrauterine adhesions, or cervical intraepithelial neoplasia.

87. A method for treating gynecological conditions comprising:

providing a solid-state laser emitting light of a wavelength of 200 to 700 nm having a laser element positioned to receive pump radiation from a pump radiation source, and the laser has a beam quality ($M^2$) that is less than or equal to 100, and delivering the laser light to tissue of a female reproductive organ.

88. The method of claim 87, wherein the light is of a wavelength that is better absorbed by said tissue than by a substance in an intermediate position between the tissue and a device used to deliver the laser light to the tissue.

89. The method of claim 87, wherein the output power density of the light delivered to the targeted tissue is high enough to vaporize the tissue.

90. The method of claim 87, wherein said delivering the laser light comprises transmitting the laser light through an optical fiber.

91. The method of claim 87, wherein the laser light has a repetition rate of between 1 Hertz and 500 Hertz.

92. The method of claim 87, wherein the optical fiber terminates in an end-firing probe emitting the laser light from an end of the optical fiber.

93. The method of claim 87, wherein the optical fiber terminates in a side-firing probe emitting the laser light in a direction transverse to the longitudinal axis of the optical fiber.

94. The method of claim 87, wherein the laser further comprises a frequency doubling element.

95. The method of claim 87, further comprising Q-switching the laser to produce a train of micropulses, each micropulse train collectively comprising a pulse.

96. The method of claim 87, wherein the pump radiation source is a laser diode.

97. The method of claim 87, wherein the pump radiation source is an arc lamp.

98. The method of claim 87, wherein the pump radiation source is a flash lamp.

99. The method of claim 87, wherein said delivering the laser light comprises transmitting the laser light through an optical fiber.

100. The method of claim 87, further comprising Q-switching the laser to produce a train of micropulses.

101. The method of claim 87, wherein said light is absorbed substantially completely by the tissue within about 1 mm of the surface, and has average irradiance in the treatment area greater than 10 kiloWatts/cm$^2$ in a spot size at least about 0.05 mm$^2$.

102. The method of claim 87, wherein said light is absorbed substantially completely by the tissue within about 1 mm of the surface, and has average irradiance in the treatment area greater than 10 kiloWatts/cm$^2$ in a spot size between about 0.1 and 0.8 mm$^2$ in the treatment area.

103. The method of claim 87, wherein said light has an irradiance of at least 30 kiloWatts/cm$^2$ in the treatment area in a spot size at least about 0.05 mm$^2$.

104. The method of claim 87, wherein the light has a wavelength and has irradiance in the treatment area sufficient to cause vaporization of a substantially greater volume of said tissue than a volume of residual coagulated tissue caused by the laser radiation.

105. The method of claim 87, wherein said tissue comprises uterine tissue, and said treatment is for a gynecological condition selected from leiomyoma uteri, rhabdomyoma, endometriosis, endometrial hyperplasia, endometrial cysts, endometrial polyps, menorrhagia, uterine septa, intrauterine adhesions, or cervical intraepithelial neoplasia.

106. The method of claim 39, 58, 60, 98 or 87, wherein the wavelength is about 532 nm.

* * * * *